United States Patent
de Guillebon et al.

(10) Patent No.: US 6,911,033 B2
(45) Date of Patent: Jun. 28, 2005

(54) MEDICAL CLIP APPLYING DEVICE

(75) Inventors: Henri de Guillebon, Manchester, MA (US); Emmanuel Manetakis, Burlington, MA (US)

(73) Assignee: Microline Pentax Inc., Beverly, MA (US)

(*) Notice: Subject to any disclaimer, the term of this patent is extended or adjusted under 35 U.S.C. 154(b) by 503 days.

(21) Appl. No.: 10/158,726

(22) Filed: May 30, 2002

(65) Prior Publication Data

US 2003/0040759 A1 Feb. 27, 2003

Related U.S. Application Data

(63) Continuation-in-part of application No. 10/085,737, filed on Feb. 28, 2002, now Pat. No. 6,840,945, which is a continuation-in-part of application No. 09/934,378, filed on Aug. 21, 2001, now Pat. No. 6,569,171.

(51) Int. Cl.$^7$ ............................................. A61B 17/10
(52) U.S. Cl. ........................ 606/142; 606/139; 606/143
(58) Field of Search ................................. 606/139, 142, 606/143, 219, 221; 227/175.1, 176.1

(56) References Cited

U.S. PATENT DOCUMENTS 5,772,673 A * 6/1998 Cuny et al. .................. 606/142

* cited by examiner

*Primary Examiner*—Julian W. Woo
(74) *Attorney, Agent, or Firm*—Greenblum & Bernstein, P.L.C.

(57) ABSTRACT

A medical clip applying device for crimping a clip onto a mammalian tissue. The clip applying device comprises a handle grip assembly having a handle and a pivotable trigger arranged onto the handle grip assembly. An elongated cartridge support channel is arranged onto a distal end of the handle grip assembly and extending through the handle grip assembly. A pair of jaws is pivotably arranged on a distal end of the elongated channel. A displacable cinch is arranged to slide onto and back from the pair of jaws to squeeze the jaws closed and to permit the jaws to bias open, respectively. A loading port is arranged on a proximal end of the handle grip assembly to permit the clip applying device to be loaded with a clip laden cartridge from the proximal end thereof.

24 Claims, 21 Drawing Sheets

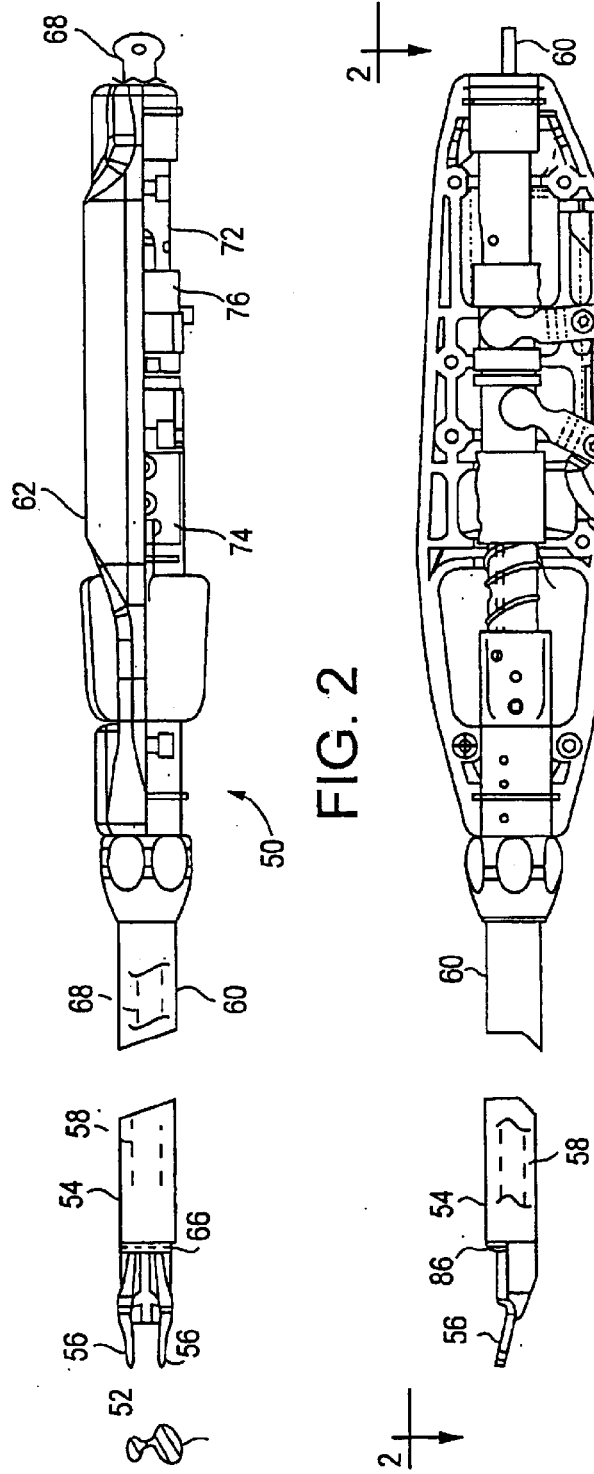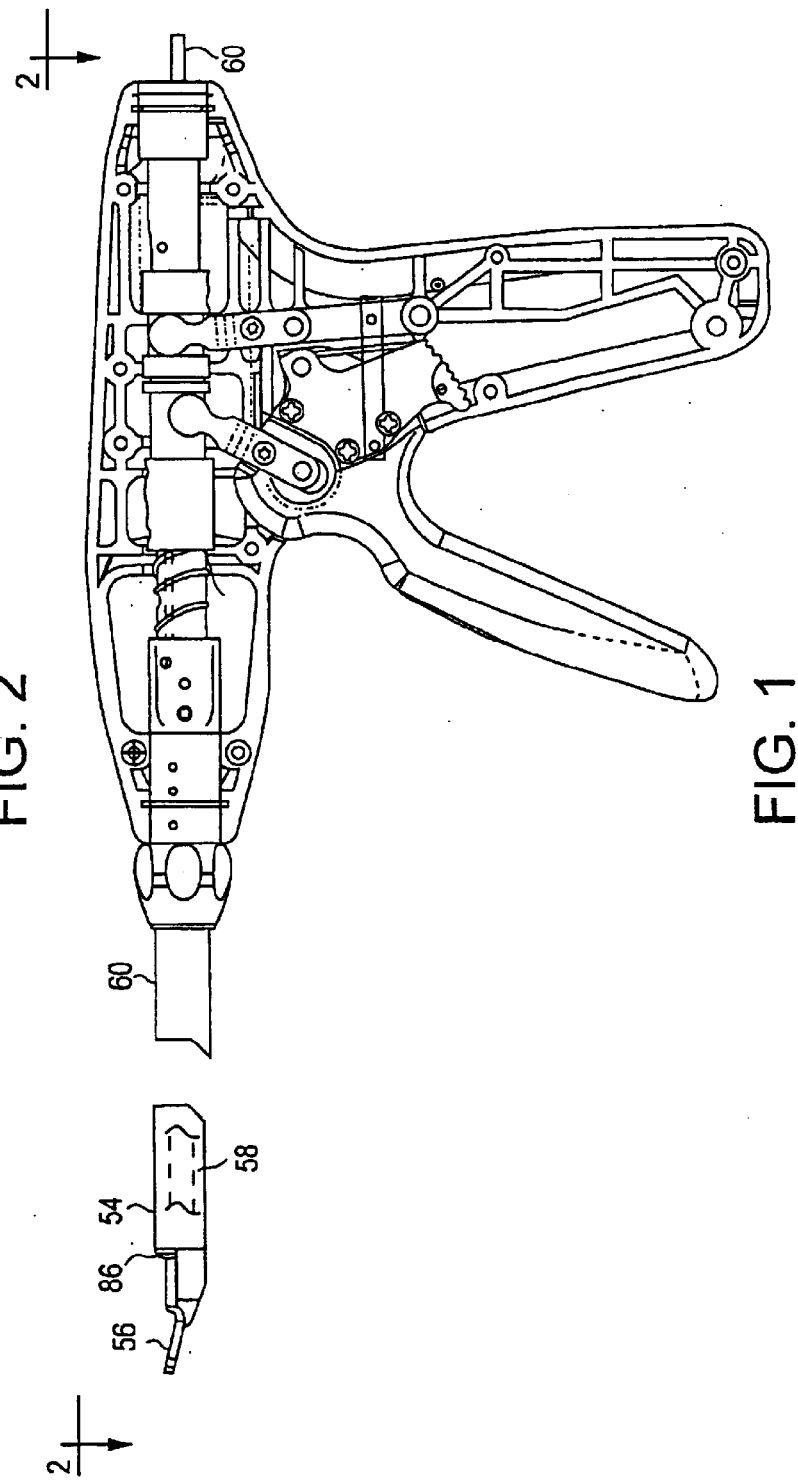

MEDICAL CLIP APPLYING DEVICE

This is a continuation-in-part application of our co-pending U.S. patent applications Ser. No. 10/085,737, filed Feb. 28, 2002, now U.S. Pat. No. 6,840,945, entitled "Medical Clip Applier Safety Arrangement", and Ser. No. 09/934,378, filed Aug. 21, 2001 U.S. Pat. No. 6,569,171 entitled "Safety Lock Mechanism for a Medical Clip Device" and each are incorporated herein by reference in their entirety.

BACKGROUND OF THE INVENTION

1. Field of the Invention

The present invention relates to clip applying devices for use in medical procedures where mammalian tissue is to be pinched and sealed in situ.

2. Prior Art

Modern surgery may be identified as laparoscopic surgery, which may be defined as minimally invasive surgery upon a patient, utilizing small or miniaturized medical devices by which body tissue is cut, removed or cauterized by small manipulable devices through small incisions or openings within the patient's body. A grasper or dissector is one such tool for that type of surgery. Such a device may be utilized to grab, dissect, treat or move tissue out of the surgical situs where other tissue may be surgically treated.

There is a need for a readily manipulable device for the grasping and or crimping/sealing of tissue by the single hand of an operating surgeon.

It is an object of the present invention to provide a re-usable tissue crimper device which is an improvement over the prior art.

It is an object of the present invention to provide an implantable medical clip device that is safer, more efficient and has the ability to maintain cleanliness during a procedure on mammalian tissue.

It is a further object of the present invention to provide a safety mechanism for such a crimper device to control the loading of such a device.

It is another object of the present invention to prevent problems of loose clips or a loose cartridge in a medical crimper device.

It is another object of the present invention to provide a crimper which will not be overloaded and wherein jamming of its jaws and/or its clips will be prevented.

It is yet another object of the present invention to provide a simple clip feed through mechanism with a safety lock which overcomes and helps avoid the problems of the prior art.

BRIEF SUMMARY OF THE INVENTION

The present invention comprises a hand manipulable clip applying device for applying medical tissue-pinching clips to mammalian tissue. The clip applying device has a patient-engaging distalmost end with a pair of squeezable jaws arranged on the distal end of an elongated channel or frame. The elongated channel is surrounded by an elongated tube, which elongated tube and elongated channel are secured at their respective proximalmost ends to the distal end of a pistol-like handle grip assembly. The handle grip assembly includes an arcuately movable squeezable trigger. By squeezing the trigger towards a housing portion of the handle grip assembly, a clip is advanced through the elongated channel and into the jaws from an elongated ladder-like clip supply cartridge disposed through the elongated housing. The actual sequence comprises the squeezing of the trigger to close the jaws and thus crimp the clip between the jaws, then releasing the trigger to advance a new clip into location between the jaws awaiting the next squeezing of the trigger. The elongated clip supply cartridge is fed into a receiving slot or port in the proximal end of the handle grip assembly.

A rotatable enclosure barrel is rotatably supported within the handle grip assembly. The rotatable enclosure barrel is connected to the proximal end of the elongated channel. The enclosure barrel has an annular distal bearing slidably disposed thereon and an annular proximal bearing slidably disposed thereon. The distal bearing has a compression spring arranged against its distalmost surface. The compression spring is also in contact with a lip of the rotatable enclosure barrel within the handle grip assembly.

The distal bearing has an elongated cinch rod extending distally therefrom. The cinch rod extends through the length of the elongated channel (and its surrounding tube). A semi-cylindrically shaped cinch is arranged on the distal end of the cinch rod. The cinch is slidably arranged on the distal end of the elongated channel and is slidably reciprocably movable outwardly of the clip-pinching jaws which are squeezably arranged on the distal end of the clip applying device. Distal and proximal movement of the cinch with respect to the elongated channel effects the respective squeezing closure and self-biased opening of the jaws at the distal end of the elongated channel. The cinch rod moves axially to slide the cinch distally and proximally corresponding to the direction of movement of the distal bearing on the distal end of the enclosure barrel. The distal bearing moves, as will be recited hereinbelow, by movement of the trigger on the handle grip assembly.

An elongated pusher rod extends adjacent to the lower side of the elongated channel. The elongated pusher rod has a proximal end connected to the proximal bearing surrounding the enclosure barrel at the proximal end of the handle grip assembly. The pusher rod has a distalmost end with a distalmost clip-engaging finger arrangement extending from one side thereof. The distalmost clip-engaging finger arrangement is movable with respect to the clip-loaded cartridge disposed within the elongated channel. Proximal motion of the distal fingers is effected by proximalmost motion of the proximal bearing around the enclosure barrel within the handle grip assembly. As the distal finger arrangement is pulled rearwardly or proximally with respect to the handle grip assembly, an arrangement of mid-portion fingers attached to the pusher rod are cammed out of the way of the clip loaded cartridge and are moved proximally, as is the distalmost clip-engaging finger arrangement with respect to the next-to-be-pinched clip within that cartridge. As the trigger in the pistol-like handle assembly is released, the proximalmost bearing is caused to advance with respect to the trigger. As the pusher rod advances, it distally advances the mid-portion fingers to cam back into a slot within the elongated channel arranged at a longitudinal midpoint of the elongated channel member, to engage a series of openings in a ladder member slideably arranged within that cartridge. The distal end of the ladder member which is engaged by the mid-portion fingers of the pusher rod thus pushes against the proximalmost or last clip in the cartridge to also push distally the next adjacent clip(s) within that cartridge. Thus forward or distal advance of the series of clips loaded within the cartridge is thus effected. Proximal (rearward) movement of the cinch by the proximal movement of the cinch rod permits the jaws to bias themselves open and the distal fingers at the distalmost end of the pusher rod pushes the next available clip into the guide slots in the opposed faces of the respective jaws as the jaws open fully as the trigger is permitted to open fully from the handle portion of the handle grip assembly. Release of the squeezed trigger will automatically advance the next available clip within the cartridge distal of the ladder in the cartridge. The pusher rod has two pusher elements, the pusher fingers in the distalmost or front end thereof and one in the mid portion thereof. The front pusher fingers advance the first clip into the jaws and the mid-portion pusher finger arrangement advancing the ladder within the cartridge, which ladder in turn pushably advances the remaining clips forward behind the first clip.

A spring is arranged within the enclosure barrel at the proximalmost end of the handle grip assembly. The spring has a slight zig-zag configuration and is arranged therein to prevent misleading of the cartridge in the wrong direction or upside down with respect to the handle grip assembly housing and the track therein which receives that cartridge. Proper loading of the cartridge requires that the spring lift itself radially upwardly and out of the way. If the cartridge containing the clips were placed upside down in the receiving slot in the proximal end of the handle grip assembly, the distalmost end of the cartridge would hit a finger element of the alignment spring and prevent further advance of the cartridge within the handle grip assembly.

The trigger on the handle grip assembly has to be in its pulled tight or "closed" position to remove the staple cartridge. In order for the ladder pusher to move proximally and the mid-portion finger arrangement ramps on the pusher rod out of the way from being within the mid-point location of the channel so the cartridge can be loaded or inserted or removed from the clip applying device. The trigger therefore must be completely squeezed tightly against the handle grip assembly. Once the cartridge is empty and the slidable ladder within that cartridge has moved as far distally as it may, there is a little biased lip arranged at a notch in the cartridge, to prevent the slideable ladder from jamming itself inside of the jaws.

A lock system inside the proximal bearing also prevents insertion or withdrawal of the cartridge unless the trigger is fully squeezed rearwardly against the handle grip assembly. The triangle or ramp on a lock key in the proximal bearing is thus pushed upwardly or radially out of the level in which the cartridge resides in the enclosure barrel.

The cartridge must be fully inserted before the trigger can be released at all. The trigger must be fully depressed or squeezed before the cartridge can be removed. This safety arrangement is effected because the mid-location pusher triangles on the pusher rod have to be cammed out of the way in order for the clip loaded cartridge to pass over them. The cartridge must be fully withdrawn or unloaded for the trigger to be released. The cartridge also has an enlarged tab on its proximalmost end to facilitate removal of the cartridge from the handle housing and it acts as a stop for the cartridge from further distal advance therewithin.

The spacial longitudinal separation of the proximal bearing and the distal bearing surrounding the enclosure barrel in the handle grip assembly may be stopped at any point thereof, due to the ratchet and pawl arrangement between the pivot plate and the ratchet finger within the handle grip assembly. This permits a clip to be held at a particular squeezed disposition prior to its final last-phase squeeze by the trigger being pulled tightly towards the handle grip assembly. Because the ratchet and pawl are bi-directional, the trigger must be fully squeezed and released before attempting to crimp the next available clip. A forward lever arm and yoke is disposed in sliding engagement with a saddle point in the distal bearing. The forward lever arm moves arcuately, in conjunction with the trigger as it is squeezed and released. A rear lever arm effects movement with a yoke engaging a saddle portion of the proximal bearing. The rear lever arm moves arcuately about a pivot axis, and causes the rear or proximal bearing to move only after the distalmost bearing has begun its advance. This is due to the delayed motion between a slotted link bar arranged between the swivel plate and the rear lever arm. A slot is arranged in the proximalmost end of the link bar which permits initial distal advance of the cinch by virtue of distal advance of the distal bearing permitted before the proximal bearing is effected its rearward or proximal motion and before any consequent pulling of the pusher bar proximally or rearwardly to otherwise get ready to push a new clip forward within the cartridge.

Thus what has been shown is a unique safety arrangement for a clip applying device wherein a pair of separate bearings are moved apart from one another and towards one another depending upon the direction of motion of a trigger attached to the handle grip assembly. The cinch, which squeezes the jaws together to squeeze a clip around a mammalian tissue moves in a one to one correspondence with the distalmost bearing. Likewise, the proximalmost bearing moves in a one to one correspondence with the pusher rod which effects advance and retraction of the pusher rod to effect sequential advance of clips between those squeezable jaws and subsequent advance of the next adjacent clip by pushing the ladder within that cartridge disposed within the elongated channel.

By virtue of the ability to load the clip applying device from its proximalmost end of its handle grip assembly, contamination of the device and clips are minimized, efficiency is maximized, and clips may be utilized and the clip applying device may be reloaded while the distalmost end of the device is still within or on the patient.

The invention thus comprises a medical clip applying device for crimping a clip onto a mammalian tissue. The device comprises a handle grip assembly having a handle and a pivotable trigger arranged onto the handle grip assembly. An elongated cartridge support channel is arranged onto a distal end of the handle grip assembly and extends through the handle grip assembly. A pair of jaws is pivotably arranged on a distal end of the elongated channel. A displacable cinch is arranged to slide onto and back from the pair of jaws to squeeze the jaws closed and to permit the jaws to bias open, respectively. A loading port is arranged on a proximal end of the handle grip assembly to permit the clip applying device to be loaded with a clip laden cartridge from the proximal end. The clip applying device may include a swivel lock arranged in the channel to secure the clip laden cartridge with respect to the channel. A pair of sequentially displaceable annular bearings are connected to the clip cartridge and to the jaws respectively, to permit advance of a clip in the cartridge prior to closing of the jaws. A biased spring is arranged in the channel to prevent improper loading of the clip laden cartridge in the channel. The trigger is movable to a squeezed closed position to permit the clip laden cartridge to be displaced with respect to the channel. The cartridge is withdrawn from the channel to permit the trigger to be released. The cartridge has an opening therein to permit the swivel lock to lockably engage the cartridge. The channel is enclosed by an enclosure barrel within the handle grip assembly. The enclosure barrel has an arrangement of slots therein to permit the bearings to connect to the jaws and to the cinch. The swivel lock has a triangular edge arranged to mate with the opening in the cartridge and to block the cartridge upon improper loading of the cartridge in the channel, and to not allow the cartridge to be withdrawn when the trigger is in the open or "un-squeezed" position.

The invention also includes a method of applying a crimped clip to mammalian tissue. The method may comprise the steps of: arranging a pair of pinchable jaws on a distal end of an elongated channel; securing a proximal end of the channel through a handle grip assembly; loading a clip laden cartridge into the proximal end of the channel at a proximal end of the handle grip assembly; squeezing a trigger connectively linked to movable annular bearings arranged about the channel; advancing a clip between the jaws as the trigger is released; and subsequently pinching the jaws closed to pinch the clip onto a tissue disposed between said jaws.

The method may also include the steps of: moving a first distal bearing distally, moving a second proximal bearing subsequent to the first bearing moving to effect advance and pinching of the clips; arranging a swivel lock in an enclosure barrel surrounding the channel to prevent the cartridge from displacement with respect to the channel during operation of the clip applying device; advancing the clips in the clip laden cartridge by elliptically cammed motion of a clip pusher engaging and disengaging a distalmost clip in the cartridge; connecting the clip pusher to the proximal bearing; and connecting a clinch to the distal bearing to permit the jaws to be squeezed together.

The invention may also include a method of loading a mammalian tissue crimping device with a plurality of crimpable clips so as to enable the crimping device to selectively, serially, crimpably apply a plurality of crimped clips to mammalian tissue, comprising the steps of: arranging a pair of pinchable jaws on a distal end of an elongated channel, the elongated channel having a proximal end which is supported through an elongated trigger handle grip assembly of the crimping device; and loading an elongated clip laden cartridge into a proximal end of the elongated channel at a loading port located at a proximal end of the trigger handle grip assembly; squeezing a trigger connectively linked to a pair of movable annular bearings arranged about the channel in the trigger handle grip assembly; advancing a clip between the jaws after the trigger is squeezed; and subsequently pinching the jaws closed to pinch the clip onto a tissue disposed between the jaws; moving a first distal bearing distally, and moving a second proximal bearing subsequent to the first bearing moving to effect advance and pinching of the clips; arranging a swivel lock in an enclosure barrel surrounding the channel to prevent the cartridge from displacement with respect to the channel during operation of the clip applying device; advancing the clips in the clip laden cartridge by elliptically cammed motion of a clip pusher engaging and disengaging a distalmost clip in the cartridge; connecting the clip pusher to the proximal bearing; and connecting a clinch to the distal bearing to permit the jaws to be squeezed together.

The invention may also include a method of applying a crimped clip to mammalian tissue, by an elongated clip applying device having a paid of squeezable jaws on a distal end thereof, and a trigger grip handle assembly at a proximal end thereof, the jaws and the trigger grip handle connected by a clip guide track and a jaw actuation mechanism, the method comprising: squeezing the trigger towards the handle assembly to pinch the jaws together and to separate a pair of drive bearings in the trigger grip handle assembly and are connected between the trigger and the jaws; releasing the trigger away from the handle to advance a clip between the jaws; squeezing the trigger towards the handle assembly to pinch the jaws and a clip pushed therebetween; and releasing the trigger pivotably away from the handle to advance a further clip between the jaws. The method includes the steps of: loading an elongated multi clip-bearing clip cartridge into the clip guide track arrangement through an opening on a proximal end of the trigger grip handle assembly; arranging a lockout mechanism in the clip guide track arrangement to prevent a misleading of the clip cartridge into the clip track arrangement.

BRIEF DESCRIPTION OF THE DRAWINGS

The objects and advantages of the present invention will become more apparent, in view of the conjunction with the following drawings in which:

FIG. 1 is a side elevational view of a clip applying device with a portion of the cover of the handle grip assembly removed;

FIG. 2 is a view taken along the lines 2—2 of FIG. 1

DETAILED DESCRIPTION OF THE PREFERRED EMBODIMENTS

Figure 3:
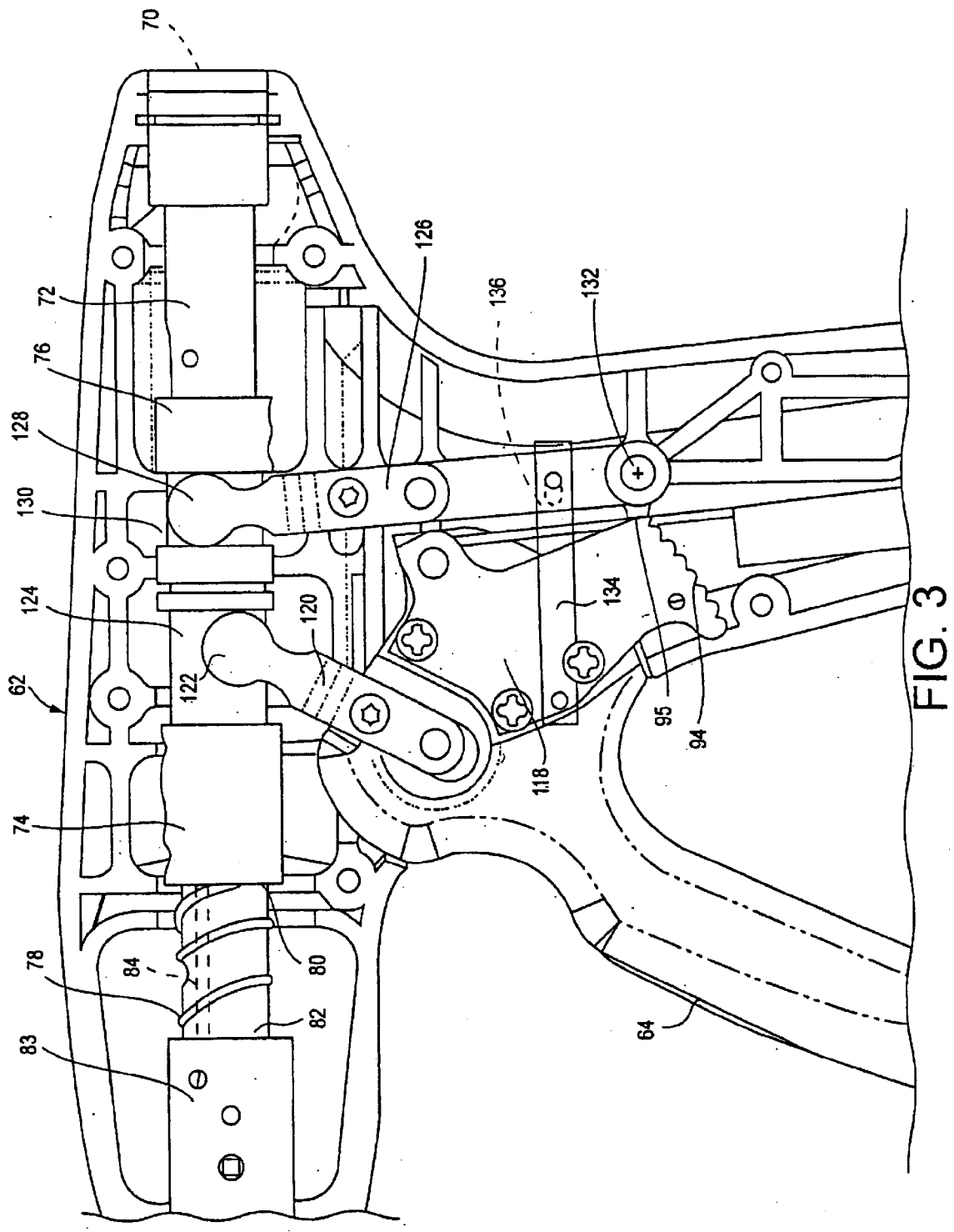
FIG. 3 is an enlarged side elevational view of the mechanism within the handle grip assembly, with the trigger shown in a fully "forward" (un-squeezed) orientation.

Referring now to the drawings in detail, and particularly to FIGS. 1 and 2 there is shown a hand manipulable clip applying device 50 for applying medical tissue-pinching clips 52 to mammalian tissue "T". The clip applying device 50 has a patient-engaging distalmost end 54 with a pair of squeezable jaws 56 arranged thereon supported on the distal end of an elongated channel or frame 58. The elongated channel 58 is surrounded by an elongated tube 60, which elongated tube 60 and elongated channel 58 are secured at their respective proximalmost ends to the distal end of a pistol-like handle grip assembly 62. The handle grip assembly 62 includes an arcuately movable squeezable trigger 64. By releasing the squeezed trigger 64 away from a housing portion 66 of the handle grip assembly 62, a clip 52 is advanced through the distal end of the elongated channel 58 and into the aforementioned jaws 56 from an elongated ladder-like clip supply cartridge 68 (as may be seen at least partially in FIGS. 1, 2, 8–12, 14–17 and 19–22), disposed through the elongated channel 58. The elongated clip supply cartridge 68 is fed into a receiving slot or port 70 in the proximal end of the handle grip assembly 62, as is shown in FIGS. 1, 2, 12, 14, 15, 16, 21 and 22.

A rotatable enclosure barrel 72 is rotatably supported within the handle grip assembly 62, as shown most clearly in FIGS. 1–7. The rotatable enclosure barrel 72 is connected to the proximal end of the elongated channel 58, as best represented in FIGS. 1 and 2. The enclosure barrel 72 has an annular distal bearing 74 slidably disposed thereon and an annular proximal bearing 76 slidably disposed thereon. The distal bearing 74 has a compression spring 78 arranged against its distalmost surface 80. The compression spring 78 is also in contact with a lip 82 of the proximal end of the rotatable support bearing 83, arranged within the handle grip assembly 62. The compression spring 78 releases the cinch 86 after the jaws 56 have been closed and a clip 52 has been crimped and also provides a proximally directed bias against the distal bearing 74.

The distal bearing 74 has an elongated cinch rod 84 (as may be seen in FIGS. 3, 4, 5, 6, 8–11) extending distally therefrom. The cinch rod 84 extends through the length of the elongated channel 58 (and its surrounding protective enclosure tube 60). A semi-cylindrically shaped cinch 86 is arranged on the distal end of the cinch rod 84, as may be seen in FIGS. 8–11. The cinch 86 is slidably arranged on the distal end of the elongated channel 58 and is reciprocably slidable outwardly of the sides of the clip-pinching jaws 56 which are squeezably arranged on the distal end of the clip applying device, as best shown in FIG. 2. Distal and proximal movement of the cinch 86 with respect to the elongated channel 58 effects the respective squeezing closure and self-biased opening of the jaws 56 at the distal end of the elongated channel 58. The cinch rod 84 moves axially to slide the cinch 86 distally and proximally corresponding to the direction of movement of the distal bearing 74 on the distal end of the enclosure barrel 72. The distal bearing 74 is biased proximally by the compression spring 78, effecting a proximal motion to the distal bearing 74, as will be recited hereinbelow, including movement of the trigger 64 relative to the handle 66 of the handle grip assembly 62.

Figure 4:
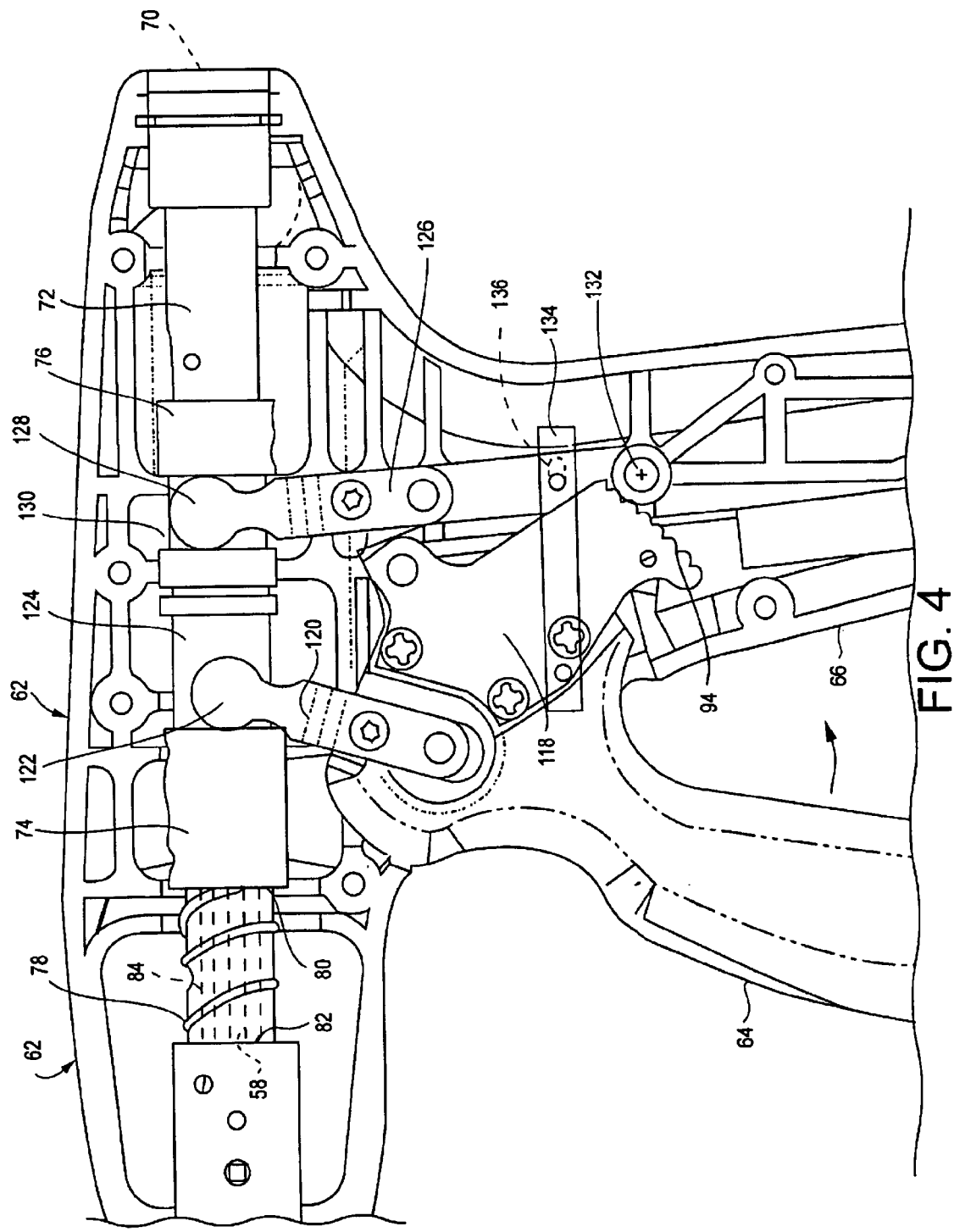
FIG. 4 is a view similar to that of FIG. 3 with the trigger in a slightly pulled or squeezed configuration with respect to the handle grip assembly.
Figure 5:
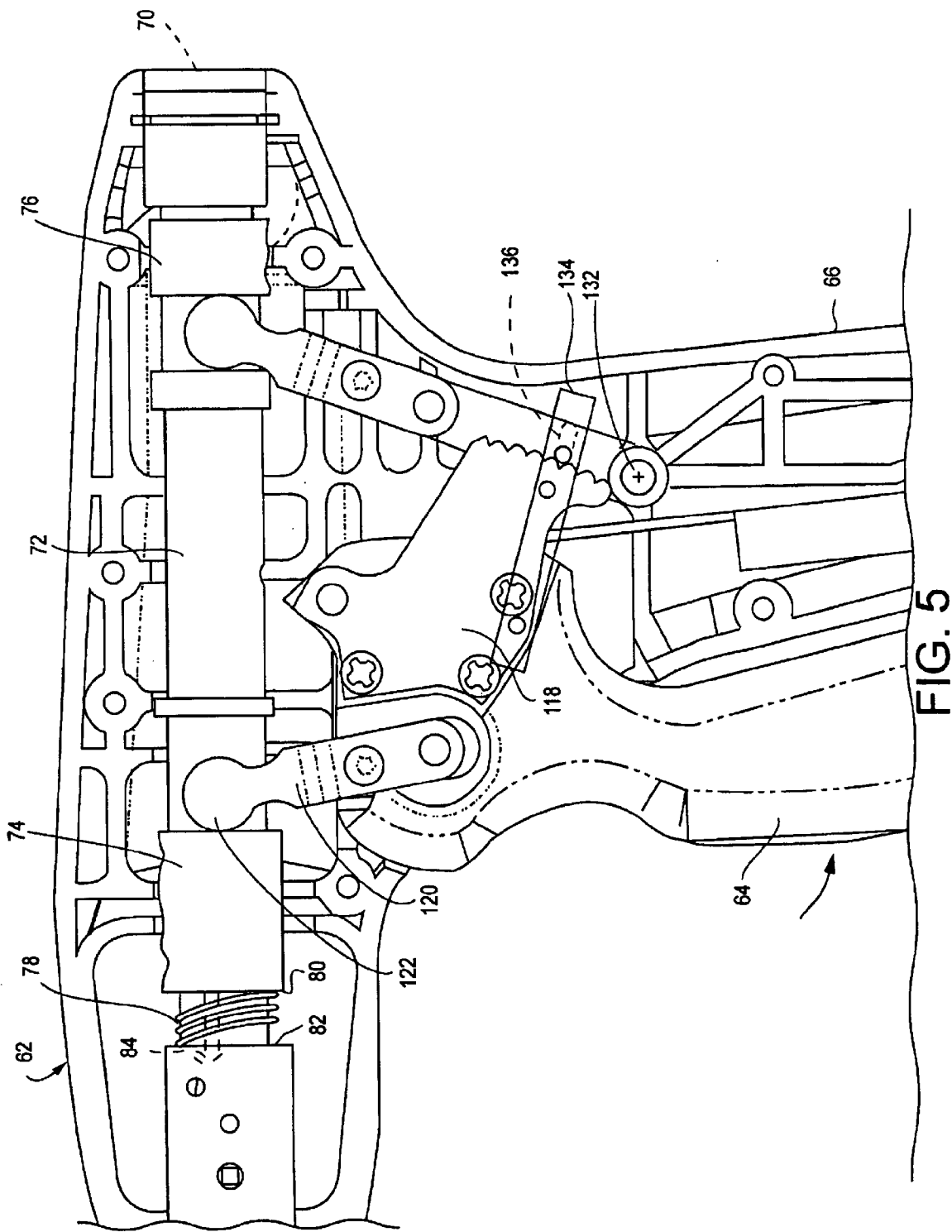
FIG. 5 is a view similar to FIG. 4 with the trigger fully "closed" or squeezed with respect to the handle grip assembly.
Figure 6:
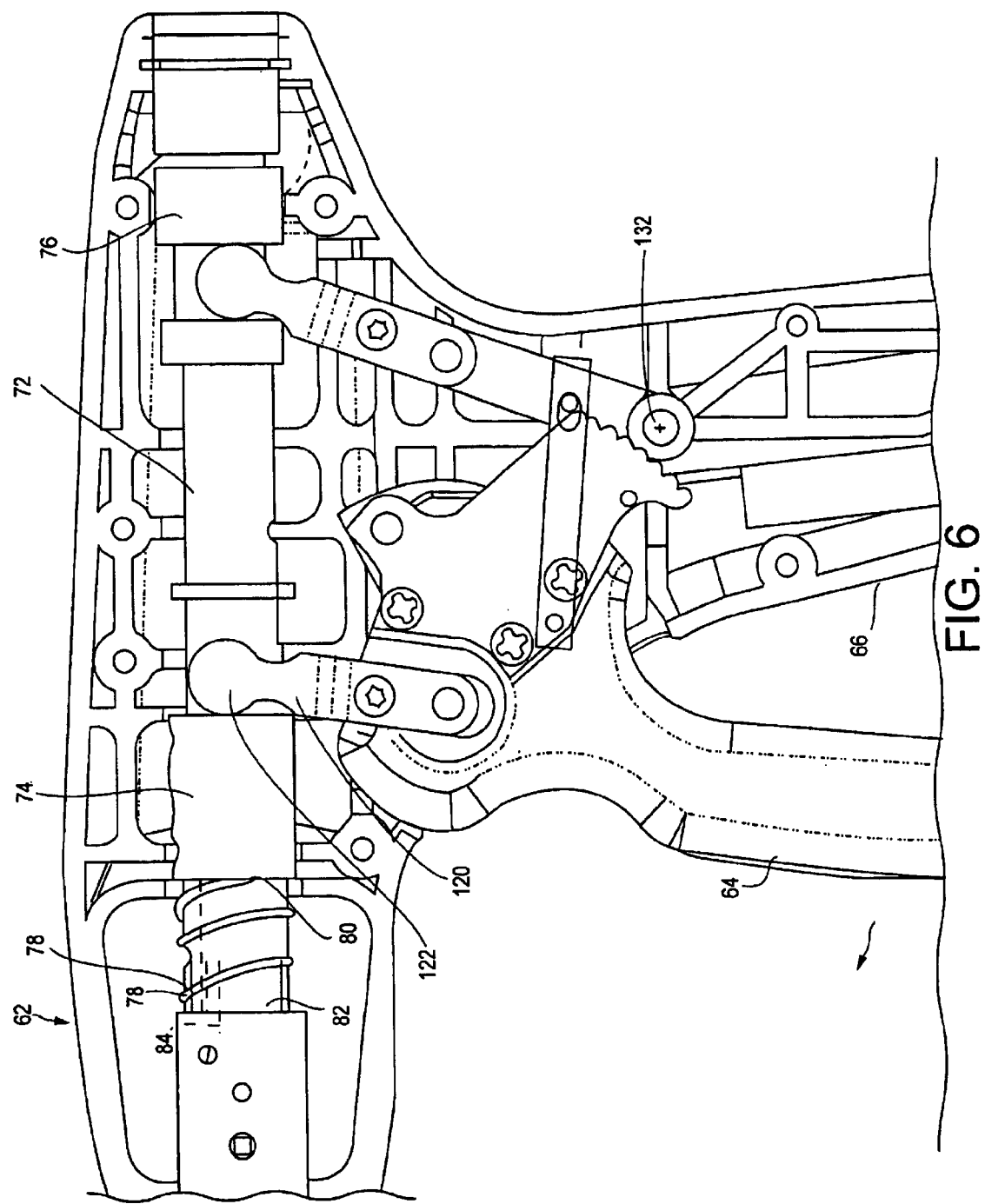
FIG. 6 is a view similar to FIG. 5 with the trigger released slightly with respect to the handle grip assembly.
Figure 7:
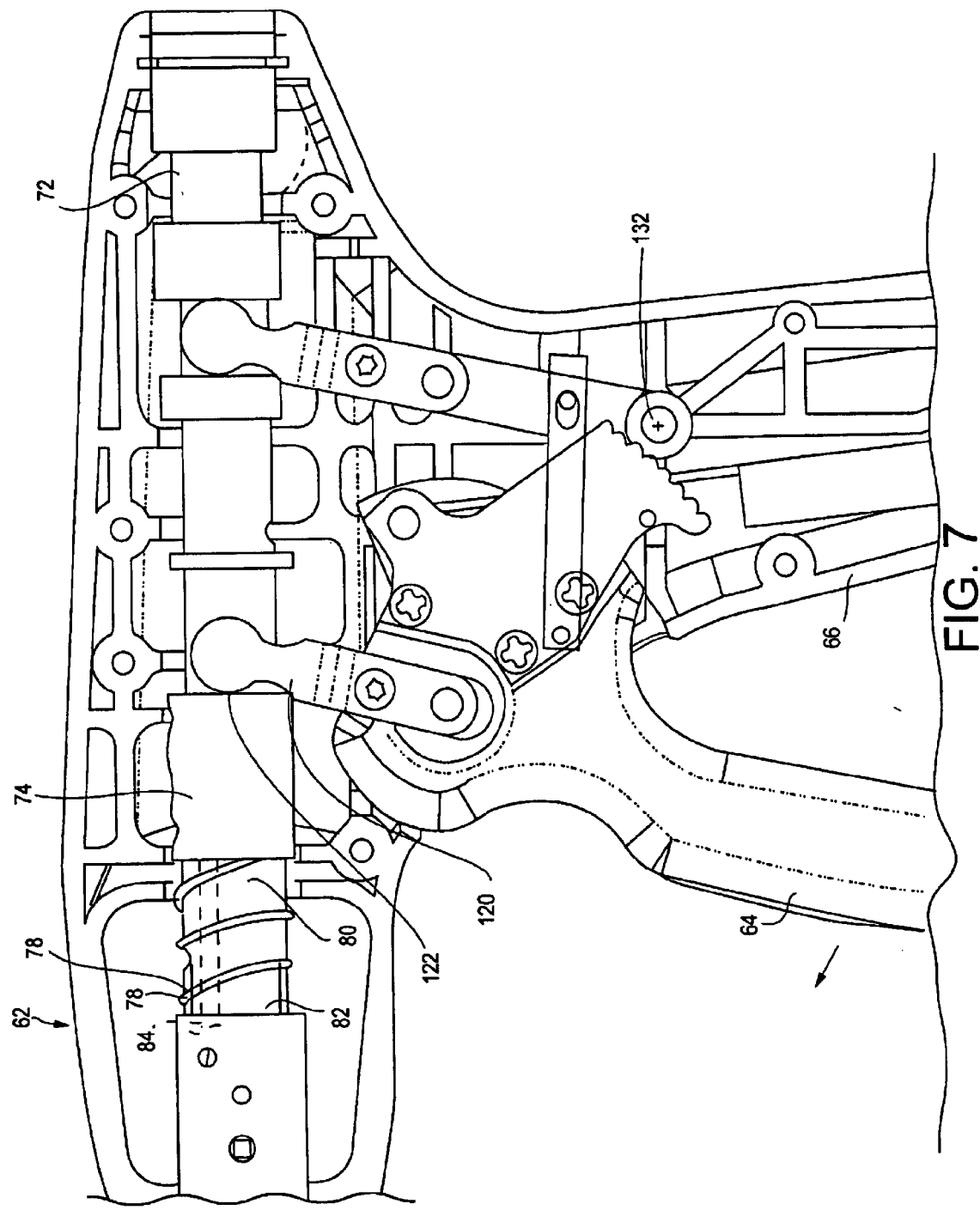
FIG. 7 is a view similar to FIG. 6 with the trigger further arcuately separated from the handle grip assembly.
Figure 8:
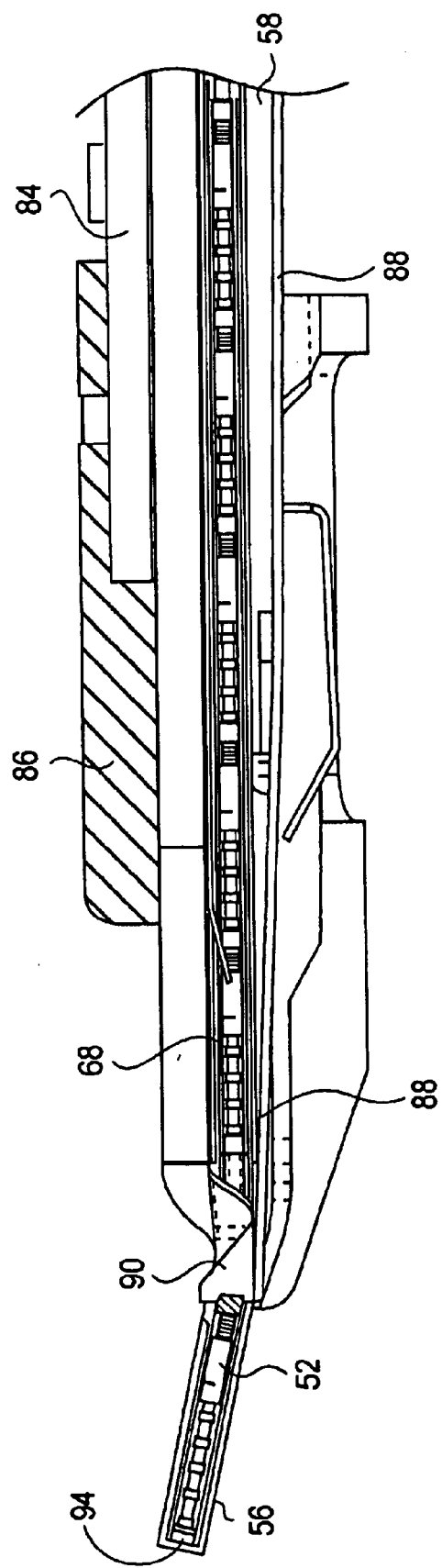
FIG. 8 is a side elevational view of the distal tip assembly of the clip applying device with the jaws fully loaded with a clip therebetween.
Figure 9:
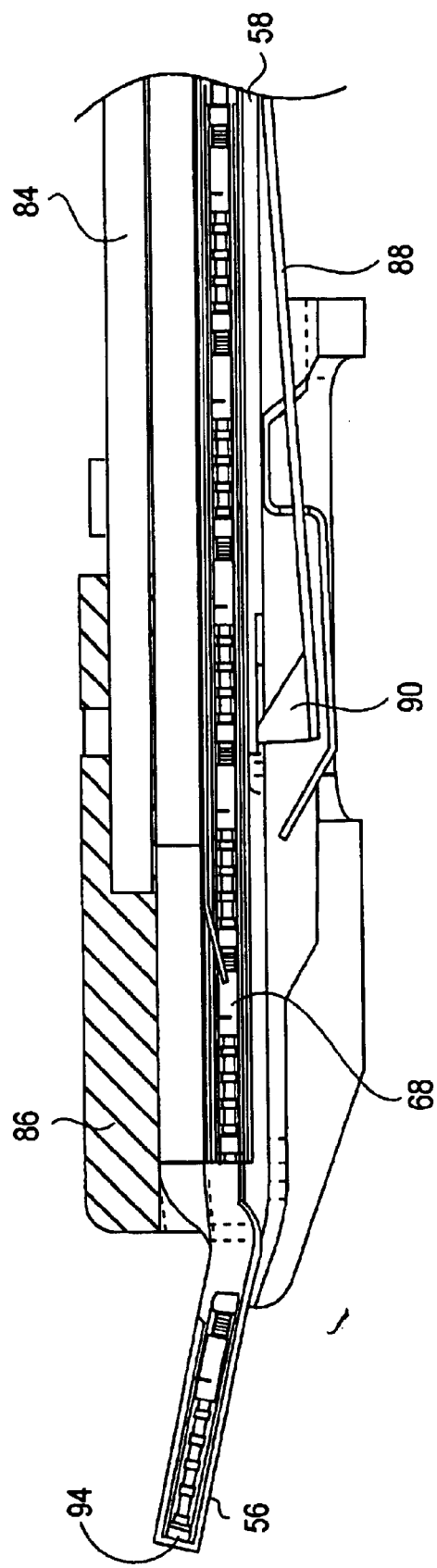
FIG. 9 is a side elevational view of the distal tip assembly shown in FIG. 8 with the cinch fully squeezing the jaws closed and thus crimping the clip.

An elongated pusher rod 88 extends adjacent to the lower side of the elongated channel 58, as is represented in FIG. 4, and in FIGS. 8–11. The elongated pusher rod 88 has a proximal end connected to the proximal bearing 76 surrounding the enclosure barrel 72 at the proximal end of the handle grip assembly 62. The pusher rod 88 has a distalmost end with a distalmost clip-engaging finger arrangement 90 extending from one side thereof, as may be seen in FIGS. 8–11. The distalmost clip-engaging finger arrangement 90 is movable with respect to the clip-loaded cartridge 68 disposed within the elongated channel 58. Proximal motion of the distal finger arrangement 90 is effected by proximalmost motion of the proximal bearing 76 around the enclosure barrel 72 within the handle grip assembly 62. As the distal finger arrangement 90 is pulled rearwardly or proximally (as represented in FIG. 9) with respect to the handle grip assembly 62 (as represented in FIGS. 4–6), an arrangement of mid-portion fingers attached to the pusher rod 88 are cammed out of the way of the clip loaded cartridge 68 and are moved proximally, as is the distalmost clip-engaging finger 90 arrangement with respect to the next-to-be-pinched clip within that cartridge 68 (as represented in FIGS. 8–9). A ratchet mechanism 94 is movably connected with the trigger 64, as may be seen in FIGS. 3–7. As the pusher rod 88 advances, it distally advances the mid-portion fingers to cam back into a slot (not shown for clarity) within the elongated channel 58 arranged at a longitudinal midpoint of the elongated channel member, to engage a series of openings in a ladder member (not shown for clarity) slidably arranged within that clip cartridge 68. The ladder member, which is engaged by the mid-portion fingers of the pusher rod 88 thus pushes against the proximalmost or last clip 52 in the cartridge 68 to also push distally the next adjacent clip(s) 52 within that cartridge 68. Thus forward or distal advance of the series of clips 52 loaded within the cartridge 68 is thus effected. Proximal (rearward) movement of the cinch 86 by the proximal movement of the cinch rod 84 permits the jaws 56 to bias themselves open and the distal fingers 90 at the distalmost end of the pusher rod 88 pushes the next available clip 52 into the guide slots 94, represented by FIGS. 8–11, in the opposed faces of the respective jaws 56 as the jaws 56 open fully, shown in FIG. 11, as the trigger 64 is permitted to open fully (see FIG. 7) from the handle 66 portion of the handle grip assembly 62. Release of the trigger 64 (after the trigger 46 has been initially squeezed against the handle 66) will automatically advance the next available clip 52 within the cartridge 68 distal of the ladder in the cartridge 68. The pusher rod 88 has two pusher elements, the pusher fingers 90 in the distalmost or front end thereof and one (not shown for clarity) in the mid portion thereof. The front pusher fingers 90 advance the first clip 52 into the jaws 56, as represented in FIG. 8, and the mid-portion pusher finger arrangement advancing the ladder within the cartridge 68, which ladder in turn pushably advances the remaining clips 52 forward behind the first clip 52.

Figure 13:
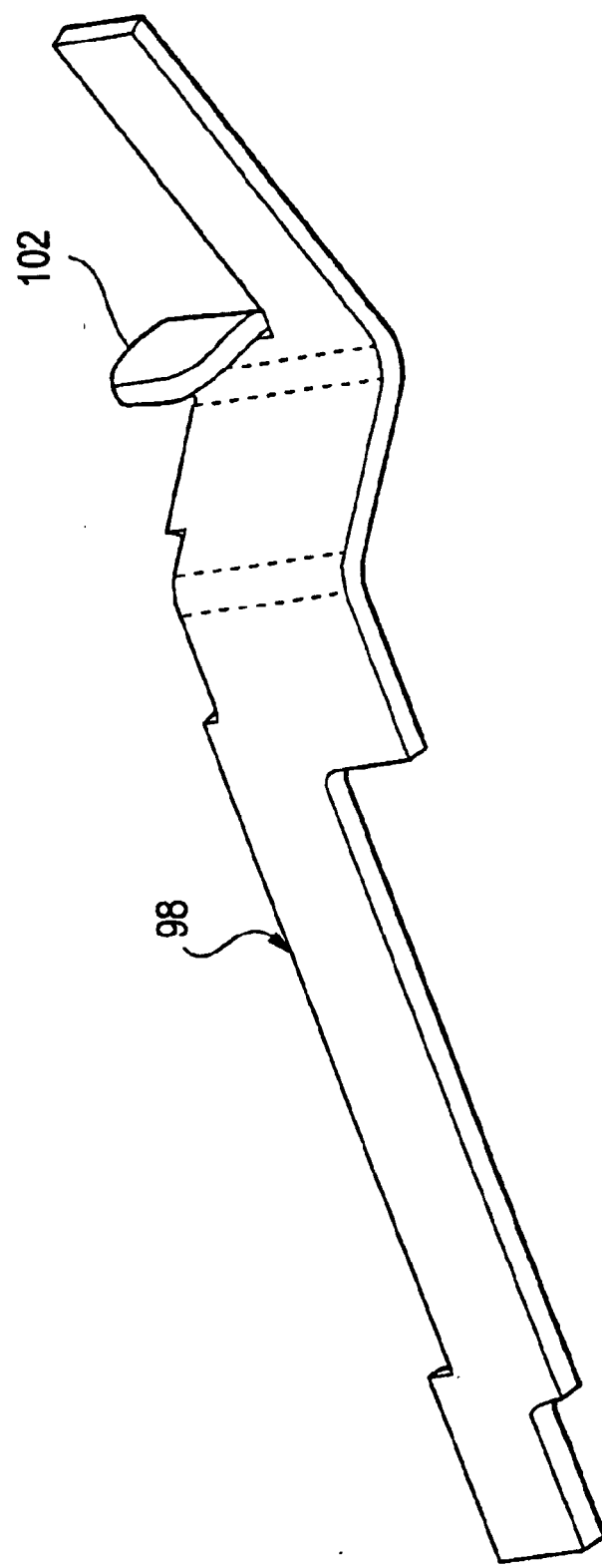
FIG. 13 is an elongated spring utilized for guiding the proper loading of a cartridge, shown here in a perspective view.
Figure 14:
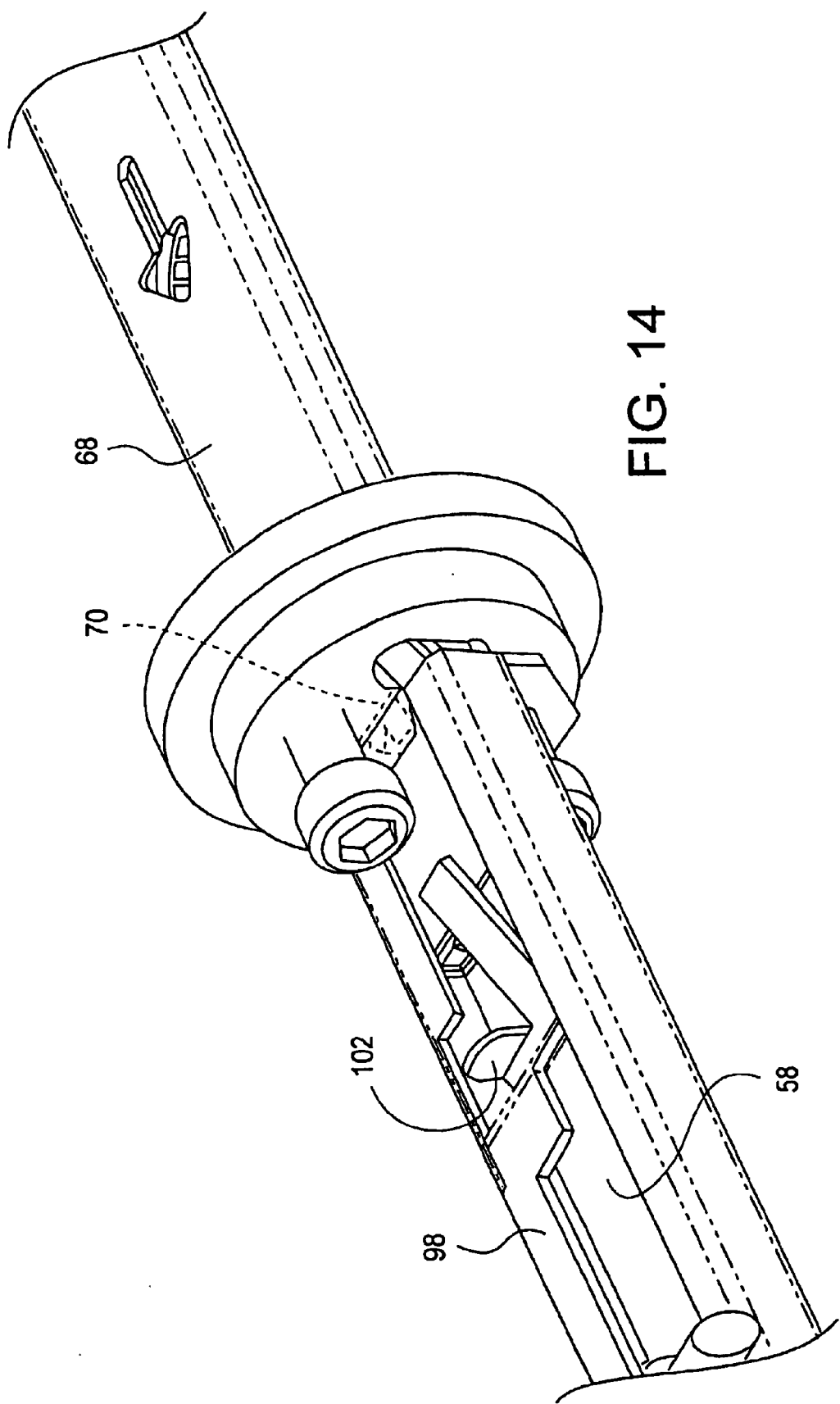
FIG. 14 is a perspective view of a cartridge being properly loaded into a portion of the proximal end of the enclosure barrel.
Figure 15:
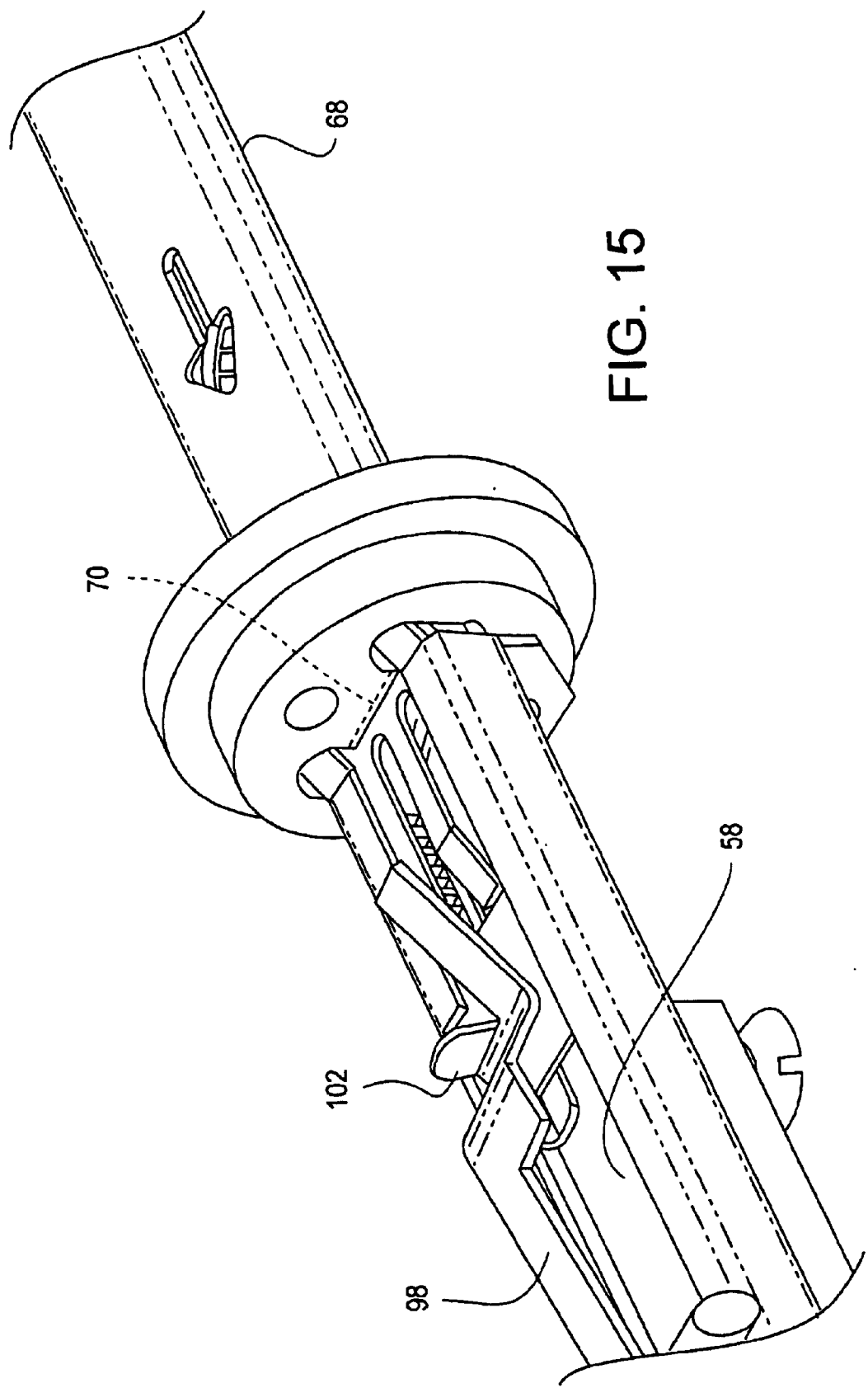
FIG. 15 is a view similar to FIG. 14 showing the cartridge being loaded and the safety spring yielding to the proper advance of that cartridge.
Figure 16:
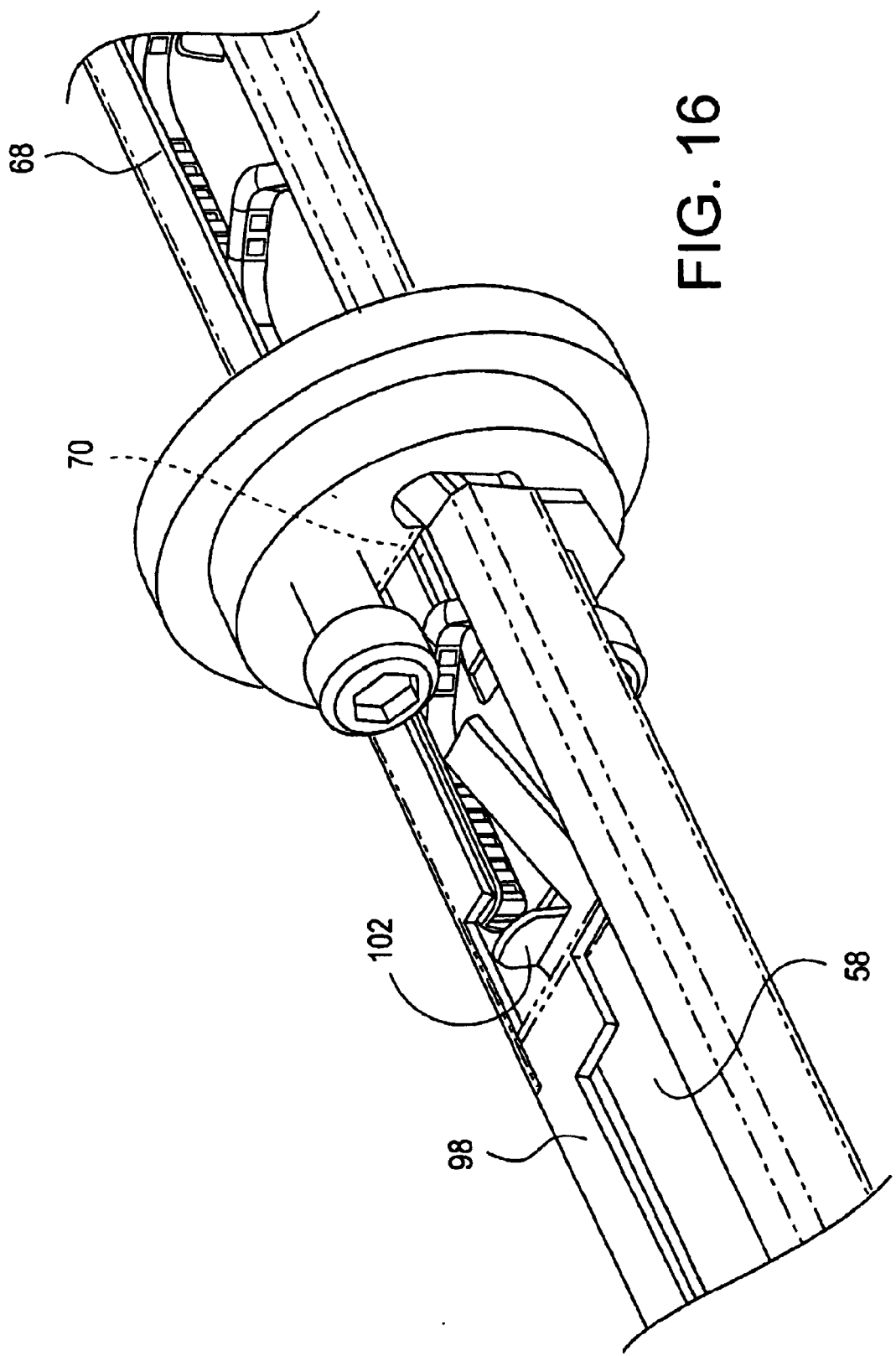
FIG. 16 is a perspective view of a cartridge being improperly loaded in the barrel at the proximal end thereof.

A bent spring 98, as shown alone in FIG. 13, is arranged within the enclosure barrel 72 (shown removed from the barrel in FIGS. 14–16) at the proximalmost end of the handle grip assembly 62. The bent spring 98 has a slight zig-zag configuration as shown in FIG. 13 et seq., and is arranged therein to prevent improper loading of the clip cartridge 68 (as is represented in FIG. 16) in the wrong direction or upside down with respect to the handle grip assembly 62 and the elongated track 58 therein, which track 58 receives that clip cartridge 68. Proper loading of the clip cartridge 68 requires that the bent spring 98 lift itself radially upwardly and out of the way, as represented in FIGS. 14 and 15. If the cartridge 68 containing the clips 52 were placed upside down in the receiving slot 70 in the proximal end of the handle grip assembly, the distalmost end of the cartridge would hit a toe "stop" element 102 of the bent spring 98 and prevent further advance of the clip cartridge 68 within the handle grip assembly 62, as represented in FIG. 16, (without its enclosure barrel 72 being shown).

The trigger 64 on the handle grip assembly 62 has to be in its pulled or squeezed tight or "closed" position, as represented in FIG. 5, to permit the insertion and the removal of a clip cartridge 68 containing the clips 52. In order for the (ladder) push rod 88 to move proximally and for the mid-portion finger arrangement to ramp the push rod 88 out of the way from being within the mid-point location of the channel 58 so the cartridge 68 can be loaded or inserted or removed from the clip applying device 50. The trigger 64 therefore must be completely squeezed tightly against the handle grip assembly 62, again as shown in FIG. 5. Once the slideable ladder within that cartridge 68 has moved as far distally as it may, there is a small biased lip arranged at a notch (not shown for clarity) in the cartridge 68, to prevent the slideable ladder from jamming itself inside of the jaws 56.

Figure 18:
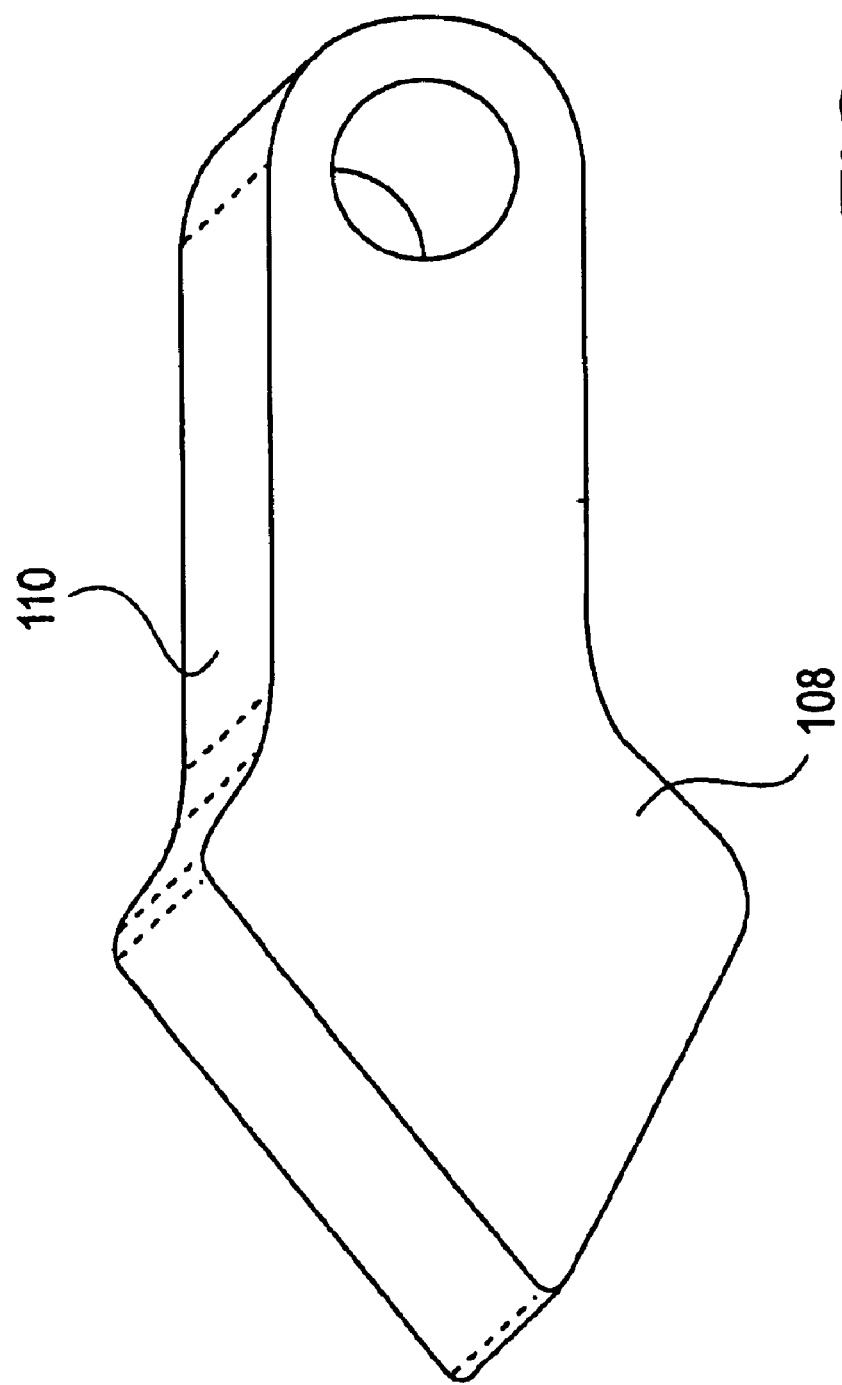
FIG. 18 shows a perspective view of a lock key which is arranged to engage a cartridge within the barrel in the proximal end of the housing.
Figure 19:
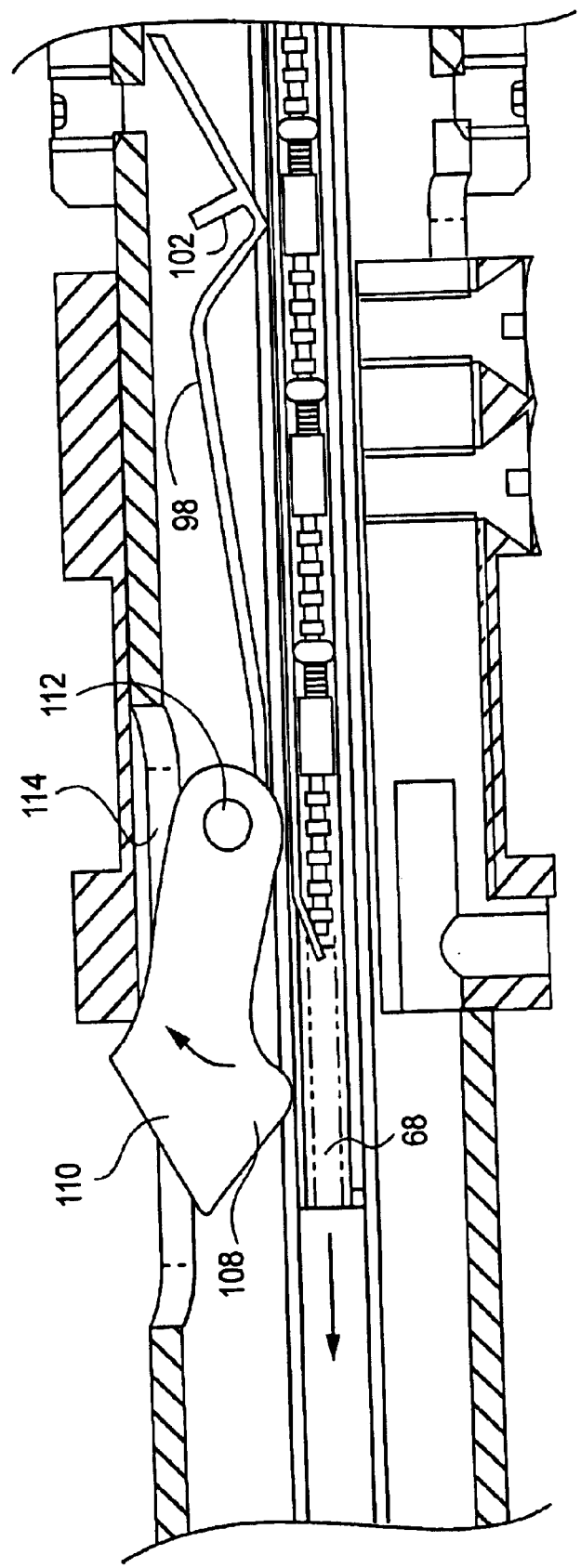
FIG. 19 is a side elevational view, in section, of the enclosure barrel with the elongated spring and the lock key arranged with respect to a cartridge being allowed to be fed therein.
Figure 20:
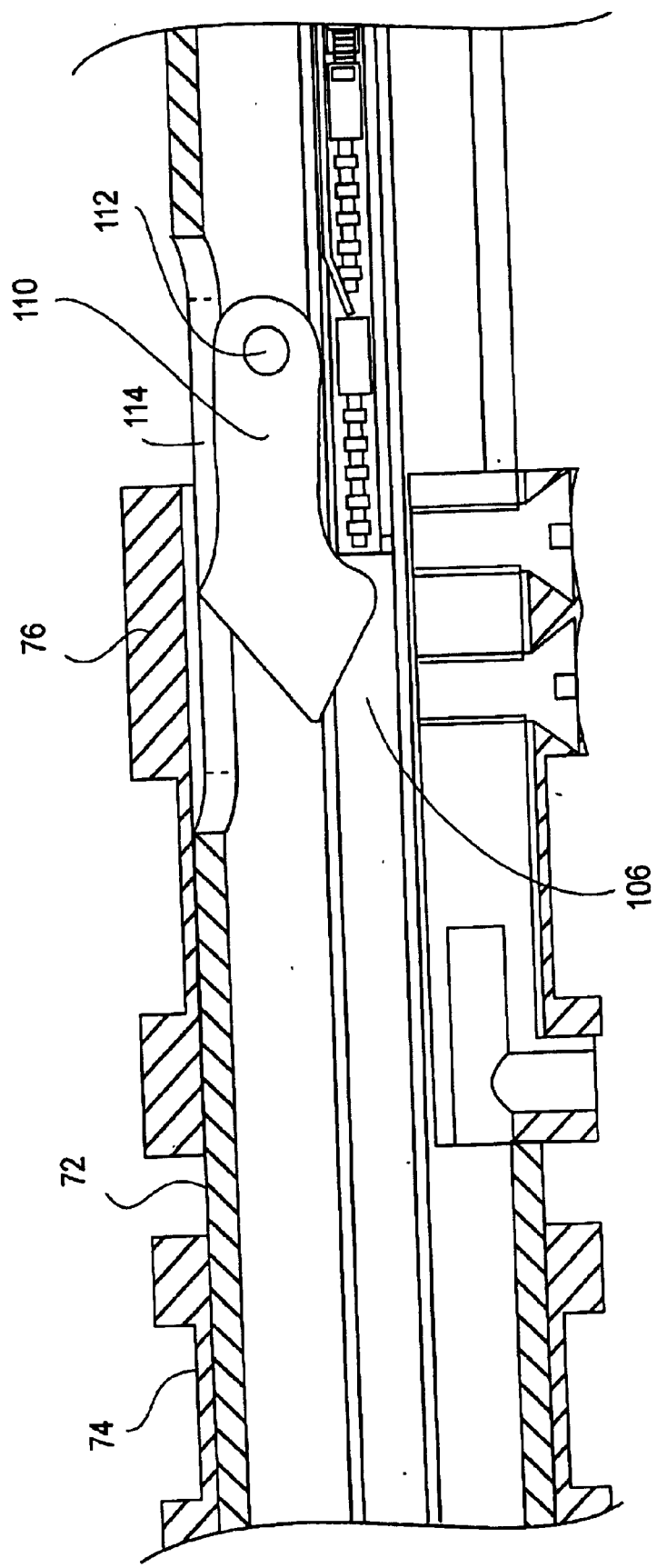
FIG. 20 is a sectional view of the barrel and sectional views of the distal and proximal bearings and the lock key stoppably engaging a cartridge which is denied passage through the barrel because the trigger is open.
Figure 21:
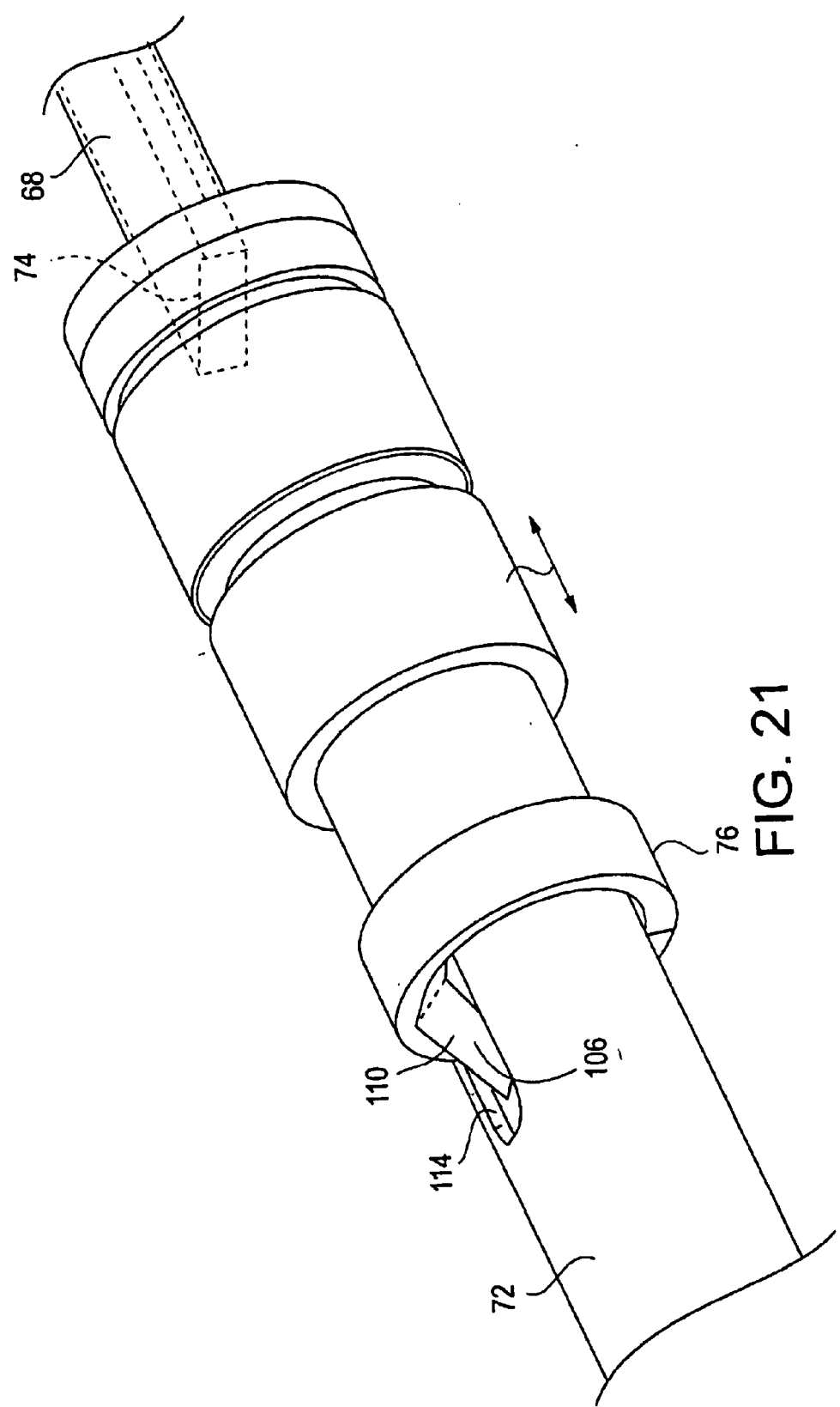
FIG. 21 is a perspective view of the barrel and the proximal bearing therearound, with a clip cartridge shown sliding through the barrel and the lock key rotated into the open slot.

A lockout system 106 is shown in FIGS. 19–22, arranged inside the enclosure barrel 72 which lock system 106 prevents insertion or withdrawal of the clip cartridge 68 unless the trigger 64 is fully squeezed rearwardly against the handle 66 of the handle grip assembly 62. The triangle or ramp 108 on a lock key 110 shown in FIG. 18, is also shown pivotably disposed on an axis 112 in the enclosure barrel 72. The lock key 110 is pushed upwardly or radially out of the level in which the cartridge 68 is pushed as it enters the enclosure barrel 72, as represented in FIG. 19. The lock key 110 is prevented from being radially displaced from the blocking position as represented in FIG. 20, by the proximal bearing 76 covering the slot 114 in the enclosure barrel 72, and thus the cartridge 68 is denied entry into the channel 58, because the handle 64 must be squeezed as shown in FIGS. 5 and 6 for the proximal bearing 76 to be axially displaced with respect to the slot 114, shown by the relative position thereof between FIGS. 20, 21 and 22.

Figure 17:
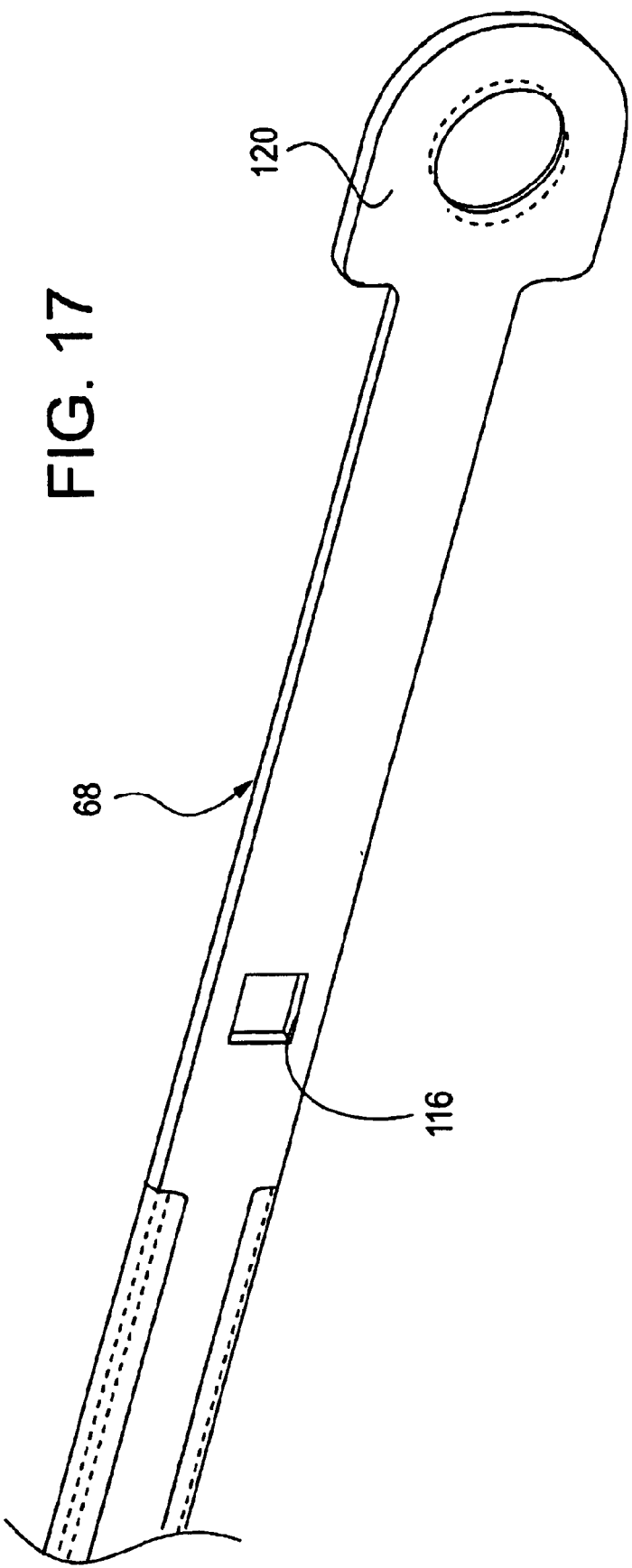
FIG. 17 shows a perspective view of the proximal end of a cartridge assembly.
Figure 22:
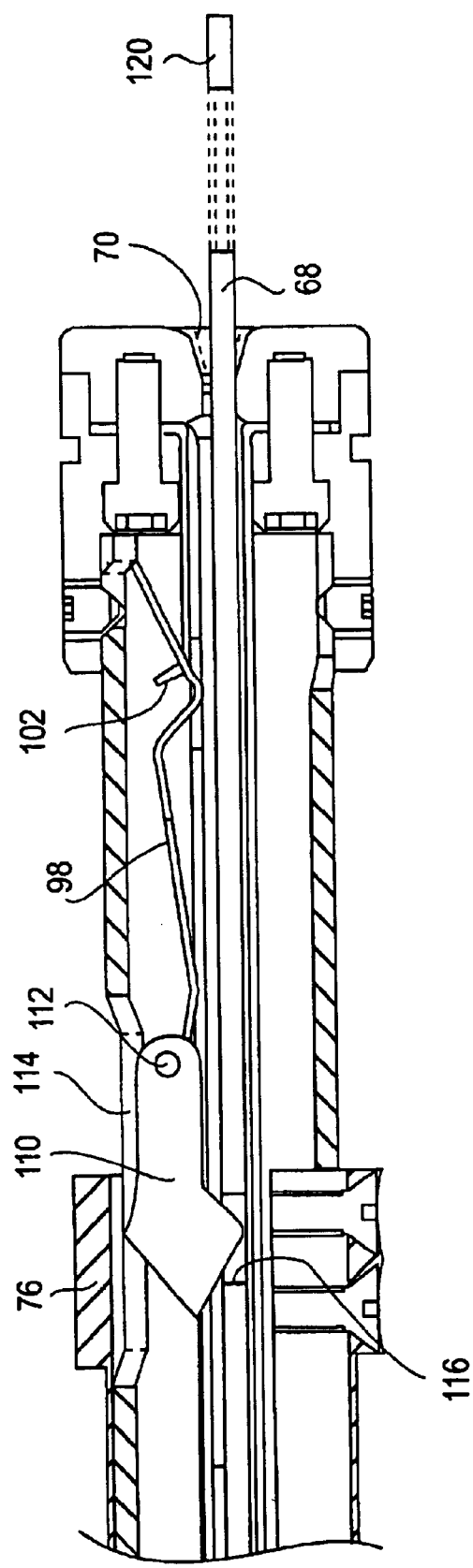
FIG. 22 is a side elevational view, in section, of the barrel and the proximal bearing therearound, with a clip cartridge fully loaded and locked therewithin and the trigger fully opened.

The cartridge 68 must be fully inserted into the device 50 before the trigger 64 can be released at all. The trigger 64 must be fully depressed or squeezed as shown in FIG. 5 before the cartridge 68 can be removed. This safety arrangement is effected because the mid-location pusher triangles on the pusher rod have to be cammed out of the way in order for the clip loaded cartridge 68 to pass over them. The cartridge 68 must be fully withdrawn or unloaded for the trigger 64 to be released. The cartridge 68 has a lock key opening 116, as shown in FIG. 17. The lock key opening 116 receives the ramp 108 and secures the cartridge 68 within the clip applying device 50 when the proximal bearing 76 is in its distalmost position, as shown in FIG. 22. This occurs when the handle 64 is in its fully open position as represented in FIG. 3.

The cartridge 68 also has an enlarged tab 120 on its proximalmost end, as shown in FIG. 17, to facilitate removal of the cartridge 68 from the handle assembly 62 to indicate that there is a cartridge 68 in place, and the tab 120 also acts as a stop for the cartridge 68 from further distal advance within the track 58.

The longitudinal separation of the proximal bearing 76 and the distal bearing 74 surrounding the enclosure barrel 72 in the handle grip assembly 62 may be stopped at any point thereof, due to the ratchet and pawl arrangement 94 and 95 between the pivot plate 118 and the pawl 95 within the handle 66 of the handle grip assembly 62. This permits a clip 52 to be held at a particular squeezed disposition prior to its final last-phase squeeze by the trigger 64 being pulled tightly towards the handle 66 of the handle grip assembly 62.

A forward lever arm 120 and a yoke 122 is disposed in sliding engagement with a saddle point 124 in the distal bearing 74, as is best seen in FIGS. 3–7. The forward lever arm 120 moves arcuately, in rigid conjunction with the trigger 64 as it is squeezed and released. A rear lever arm 126 effects movement with a yoke 128 engaging a saddle portion 130 of the proximal bearing 76. The rear lever arm 126 moves arcuately about a pivot axis 132, and causes the rear or proximal bearing 76 to move only after the distalmost bearing 74 has begun its distal advance. This is due to the delayed motion between a slotted link bar 134 arranged between the pivot plate 118 and the rear lever arm 126. A slot 136 is arranged in the proximalmost end of the link bar 134 which permits initial distal advance of the cinch 86 by virtue of distal advance of its connected distal bearing 74 permitted before the proximal bearing 76 is effected its rearward or proximal motion and before any consequent pulling of the pusher bar 88 proximally or rearwardly to otherwise get ready to push a new clip 52 forward within its cartridge 68.

Figure 10:
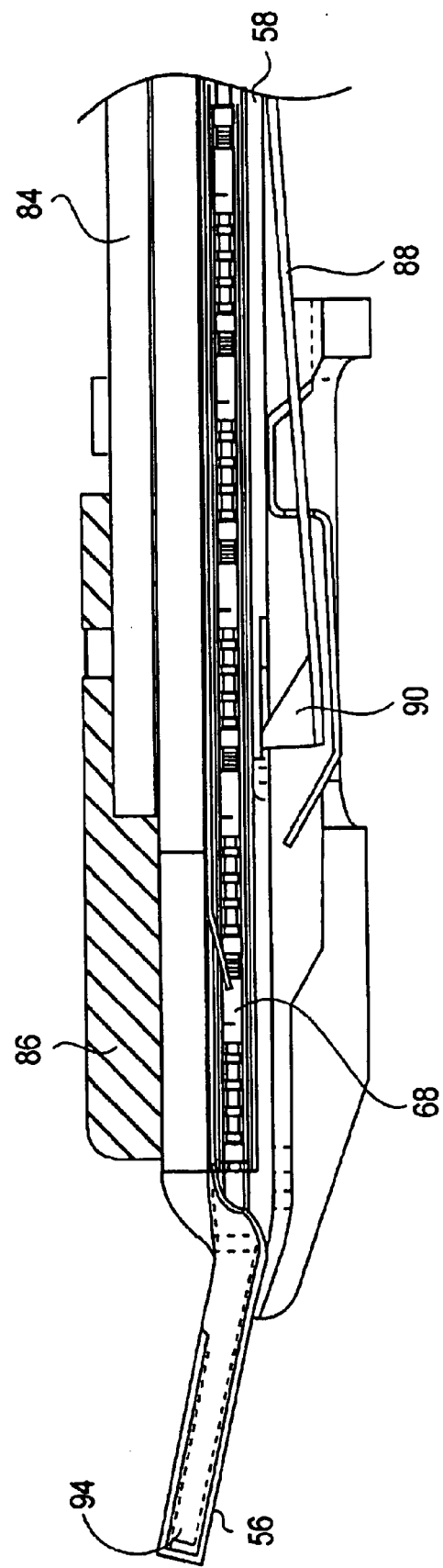
FIG. 10 is a view similar to FIG. 9 with the cinch shown partially retracted proximally.
Figure 11:
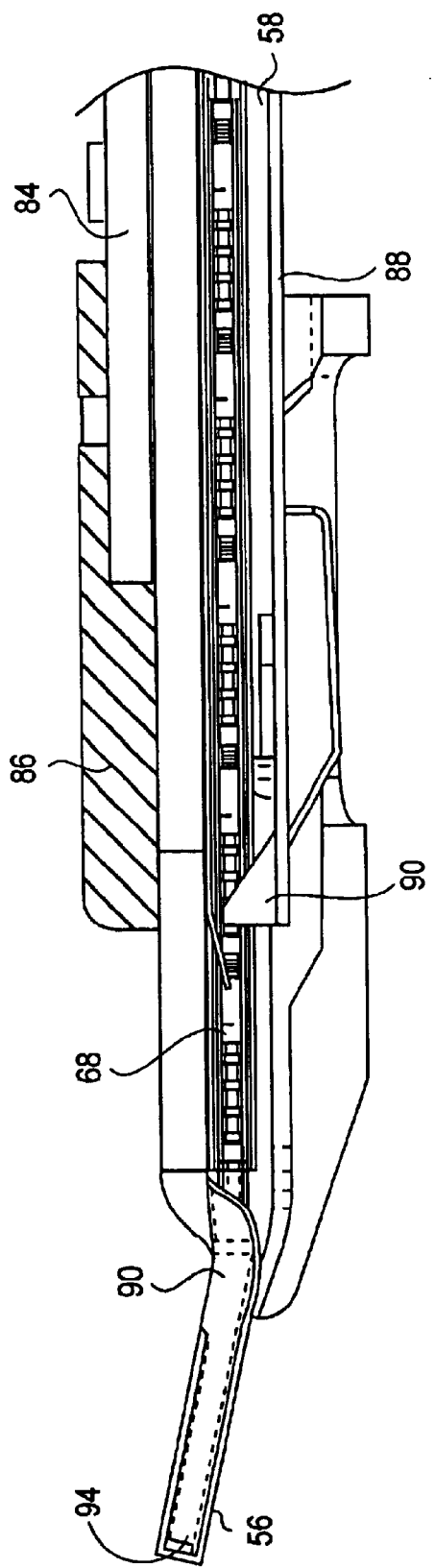
FIG. 11 is a view similar to FIG. 10 with the cinch fully retracted from the distal tip of the device and the bar feeder begins to make contact with the clip in a distal movement.
Figure 12:
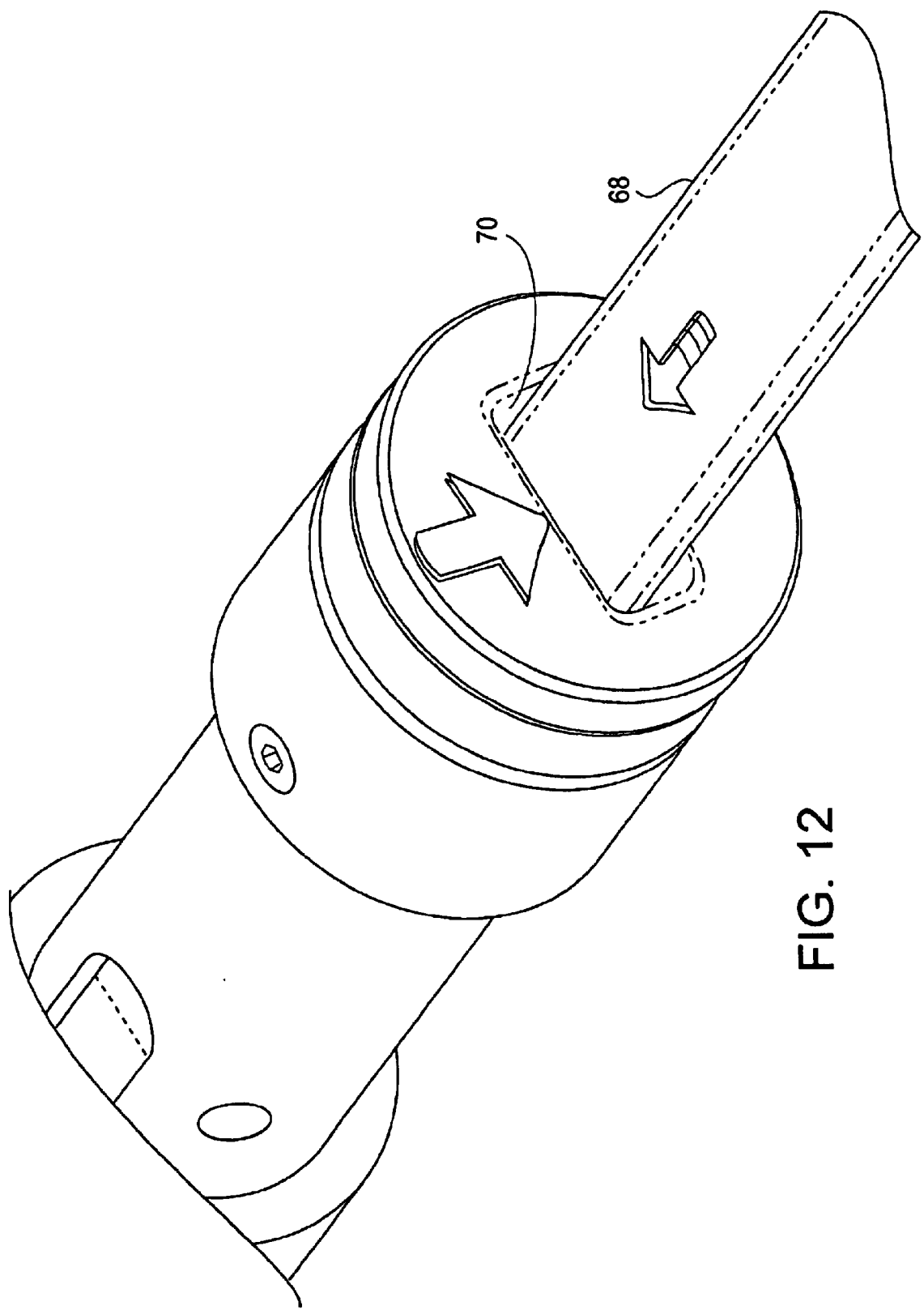
FIG. 12 is perspective view of a the proximal end of an enclosure barrel (normally positioned within the handle grip assembly) and a cartridge being fed into a loading port therein, to show the clip cartridge loading procedure.

A full cycle of the clip applying device 50 of the present invention may be appreciated by displaying the orientation of the trigger 64, and its relationship to the jaws 56 and the other associated components by reference to the drawings as follows:

Step 1—FIG. 3 shows the trigger 64 fully open and "un-squeezed", which corresponds to FIGS. 2 and 8, showing the jaws 56 fully spread apart, waiting for a tissue "T" and a clip 52 being disposed between those jaws 56 (unless the device is in its first cycle);

Step 2—FIG. 4 shows the trigger 64 in a partially "squeezed" orientation, the cinch 86 begins to move distally and begins to close the jaws 56, the pusher fingers 90 begin to move proximally, and the distal and proximal bearings 74 and 76 begin to move apart, as may be visualized in FIG. 8;

Step 3—FIG. 5 shows the trigger 64 fully squeezed against the handle 66, and thus the jaws 56 are fully pinched closed by the fully distally advanced cinch 86 as represented in FIG. 9 and the clip is fully crimped;

Step 4—FIG. 6 shows the trigger 64 partially released, and in FIG. 10, the cinch 86 beginning its proximal motion, thus permitting the jaws 56 to begin opening, the distal bearing 74 beginning to move proximally, the proximal bearing 76 beginning to move distally thus causing the pusher fingers 90 to begin move distally getting ready to pick up a new clip 52 from under the track 58;

Step 5—FIG. 7 shows the trigger 64 almost fully released, correspondingly with the distal bearing 74 moved rearwardly as far as it will go, the proximal bearing 76 still moving forwardly to effect distal advance of the pusher fingers 90 as shown in FIG. 11, to push a now engaged clip 52 distally; and Step 6—FIG. 3 shows the trigger 64 fully released, and in FIGS. 2 and 8, the jaws 56 fully open because the cinch 86 is pulled fully proximally to release them, and a new clip 52 pushed disposed between those jaws 56 by the finger pushers 90, the clip 52 and jaws 56 awaiting the cycle to begin anew.

Thus what has been shown is a unique safety arrangement for a clip applying device wherein a pair of separate bearings are moved apart from one another and towards one another depending upon the direction of motion of a trigger attached to the handle grip assembly. The cinch, which squeezes the jaws together to squeeze a clip around a mammalian tissue moves in a one to one correspondence with the distalmost bearing. Likewise, the proximalmost bearing moves in a one to one correspondence with the pusher rod which effects advance and retraction of the pusher rod to effect sequential advance of clips between those squeezable jaws and subsequent advance of the next adjacent clip by pushing the ladder within that cartridge disposed within the elongated channel.

By virtue of the ability to load the clip applying device from its proximalmost end of its handle grip assembly, contamination of the device and clips are minimized, efficiency is maximized, and clips may be utilized and the clip applying device may be reloaded while the distalmost end of the device is still within or on the patient.

We claim:

1. A medical clip applying device for crimping a clip onto a mammalian tissue, comprising:
   a handle grip assembly having a handle and a pivotable trigger arranged onto said handle grip assembly;
   an elongated cartridge support channel arranged onto a distal end of said handle grip assembly and extending through said handle grip assembly;
   a pair of jaws pivotably arranged on a distal end of said elongated channel;
   a displaceable cinch arranged to slide onto and back from said pair of jaws to squeeze said jaws closed and to permit said jaws to bias open, respectively; and
   a loading port on a proximal end of said handle grip assembly to permit said clip applying device to be loaded with a clip laden cartridge from said proximal end.

2. The clip applying device as recited in claim 1, including a swivel lock arranged in said channel to secure said clip laden cartridge with respect to said channel.

3. The clip applying device as recited in claim 2, wherein said cartridge has an opening therein to permit said swivel lock to lockably engage said cartridge.

4. The clip applying device as recited in claim 3, wherein said swivel lock has a triangular edge arranged to mate with said opening in said cartridge and to block said cartridge upon improper loading of said cartridge in said channel.

5. The clip applying device as recited in claim 1, including a pair of sequentially displaceable annular bearings connected to said clip cartridge and to said jaws respectively, to permit advance of a clip in said cartridge prior to closing of said jaws.

6. The clip applying device as recited in claim 5, wherein said channel is enclosed by an enclosure barrel within said handle grip assembly.

7. The clip applying device as recited in claim 6, wherein said enclosure barrel has an arrangement of slots therein to permit said bearings to connect to said jaws and to said cinch.

8. The clip applying device as recited in claim 1, including a biased spring arranged in said channel to prevent improper loading of said clip laden cartridge in said channel.

9. The clip applying device as recited in claim 1, wherein said trigger is movable to a squeezed closed position to permit said clip laden cartridge to be displaced with respect to said channel.

10. The clip applying device as recited in claim 1, wherein said cartridge is withdrawn from said channel to permit said trigger to be released.

11. A method of applying a crimped clip to mammalian tissue, comprising:
    arranging a pair of pinchable jaws on a distal end of an elongated channel;
    securing a proximal end of said channel through a handle grip assembly;
    loading a clip laden cartridge into said proximal end of said channel at a proximal end of said handle grip assembly;
    squeezing a trigger connectively linked to movable annular bearings arranged about said channel;
    advancing a clip between said jaws when said trigger is released; and
    subsequently pinching said jaws closed to pinch said clip onto a tissue disposed between said jaws.

12. The method as recited in claim 11, including:
    moving a first distal bearing distally, and
    moving a second proximal bearing subsequent to said first bearing moving to effect advance and pinching of said clips.

13. The method as recited in claim 11, including:
    arranging a swivel lock in an enclosure barrel surrounding said channel to prevent said cartridge from displacement with respect to said channel during operation of said clip applying device.

14. The method as recited in claim 11, including:
    advancing said clips in said clip laden cartridge by elliptically cammed motion of a clip pusher rod engaging and disengaging a distalmost clip in said cartridge.

15. The method as recited in claim 14, including:
    connecting said clip pusher rod to said proximal bearing; and
    connecting a clinch to said distal bearing to permit said jaws to be squeezed together.

16. A method of loading a mammalian tissue crimping device with a plurality of crimpable clips so as to enable said crimping device to selectively, serially, crimpably apply a plurality of crimped clips to mammalian tissue, comprising the steps of:
    arranging a pair of pinchable jaws on a distal end of an elongated channel, said elongated channel having a proximal end which is supported through an elongated trigger handle grip assembly of said crimping device; and
    loading an elongated clip laden cartridge into a proximal end of said elongated channel at a loading port located at a proximal end of said trigger handle grip assembly.

17. The method as recited in claim 16, including the step of:
    squeezing a trigger connectively linked to a pair of movable annular bearings arranged about said channel in said trigger handle grip assembly;
    advancing a clip between said jaws after said trigger is squeezed; and subsequently pinching said jaws closed to pinch said clip onto a tissue disposed between said jaws.

18. The method as recited in claim 16, including:

moving a distal bearing distally, and moving a proximal bearing subsequent to said first bearing moving to effect advance and pinching of said clips.

19. The method as recited in claim 16, including:

arranging a swivel lock in an enclosure barrel surrounding said channel to prevent said cartridge from displacement with respect to said channel during operation of said clip applying device.

20. The method as recited in claim 16, including:

advancing said clips in said clip laden cartridge by elliptically cammed motion of a clip pusher engaging and disengaging a distalmost clip in said cartridge.

21. The method as recited in claim 16, including:

connecting said clip pusher to said proximal bearing; and connecting a clinch to said distal bearing to permit said jaws to be squeezed together.

22. A method of applying a crimped clip to mammalian tissue, by an elongated clip applying device having a pair of squeezable jaws on a distal end thereof, and a trigger grip handle assembly at a proximal end thereof, said jaws and said trigger grip handle connected by a cartridge guide track and a jaw actuation mechanism, said method comprising:

squeezing said trigger towards said handle assembly to pinch said jaws together and to separate a pair of drive bearings in said trigger grip handle assembly and connected between said trigger and said jaws;

releasing said trigger away from said handle to advance a clip between said jaws;

squeezing said trigger towards said handle assembly to pinch said jaws and a clip pushed therebetween; and releasing said trigger pivotably away from said handle to advance a further clip between said jaws.

23. The method as recited in claim 22, including the step of:

loading an elongated multi clip-bearing clip cartridge into said cartridge guide track arrangement through an opening on a proximal end of said trigger grip handle assembly.

24. The method as recited in claim 23, including the step of:

arranging a lockout mechanism in said clip guide track arrangement to prevent a misloading of said clip cartridge into said cartridge track arrangement.

* * * * *